United States Patent
Rabinovitz et al.

(10) Patent No.: US 8,911,368 B2
(45) Date of Patent: Dec. 16, 2014

(54) DEVICE, SYSTEM AND METHOD FOR DETECTION OF BLEEDING

(75) Inventors: Elisha Rabinovitz, Haifa (IL); Amit Pascal, Haifa (IL); Ori Braun, Palo Alto, CA (US); Zvika Gilad, Haifa (IL); Osnat Sella-Tavor, Kfar-Kish (IL); Yaniv Birnboim, Shaarey-Tikva (IL)

(73) Assignee: Given Imaging, Ltd., Yoqneam (IL)

( * ) Notice: Subject to any disclaimer, the term of this patent is extended or adjusted under 35 U.S.C. 154(b) by 23 days.

(21) Appl. No.: 13/146,482

(22) PCT Filed: Jan. 31, 2010

(86) PCT No.: PCT/IL2010/000079
§ 371 (c)(1),
(2), (4) Date: Jul. 27, 2011

(87) PCT Pub. No.: WO2010/086859
PCT Pub. Date: Aug. 5, 2010

(65) Prior Publication Data
US 2011/0306855 A1 Dec. 15, 2011

Related U.S. Application Data

(60) Provisional application No. 61/148,319, filed on Jan. 29, 2009.

(51) Int. Cl.
| | |
|---|---|
| *A61B 5/05* | (2006.01) |
| *A61B 5/07* | (2006.01) |
| *A61B 5/00* | (2006.01) |
| *A61B 5/02* | (2006.01) |
| *A61B 5/145* | (2006.01) |
| *A61B 5/1459* | (2006.01) |

(52) U.S. Cl.
CPC .............. *A61B 5/073* (2013.01); *A61B 5/6861* (2013.01); *A61B 5/02042* (2013.01); *A61B 5/0075* (2013.01); *A61B 5/14542* (2013.01); *A61B 5/14539* (2013.01); *A61B 5/0071* (2013.01); *A61B 5/0086* (2013.01); *A61B 5/1459* (2013.01); *A61B 2560/0406* (2013.01); *A61B 5/0084* (2013.01); *A61B 2562/0238* (2013.01)
USPC ........................................................ 600/309

(58) Field of Classification Search
USPC ......... 600/117, 118, 160, 310, 343, 473, 476, 600/562, 573, 575, 582, 584, 587, 593; 128/903
See application file for complete search history.

(56) References Cited

U.S. PATENT DOCUMENTS

| | | | |
|---|---|---|---|
| 4,278,077 A | 7/1981 | Mizumoto | |
| 5,604,531 A | 2/1997 | Iddan et al. | |

(Continued)

FOREIGN PATENT DOCUMENTS

| | | |
|---|---|---|
| DE | 344 0177 | 11/1984 |
| JP | 1992-144533 | 5/1992 |

OTHER PUBLICATIONS

International Search Report for International Application No. PCT/IL2010/000079 dated Jun. 3, 2010.

(Continued)

*Primary Examiner* — Elmer Chao
(74) *Attorney, Agent, or Firm* — Pearl Cohen Zedek Latzer Baratz LLP

(57) ABSTRACT

A device, system and method for detecting bile and blood are provided. The device may comprise a housing having a gap through which in-vivo fluids may flow, illumination sources on one side of the gap, a light detector which is facing the illumination sources and is positioned on the opposite side of the gap for detecting light which passes through the in-vivo fluids, and a transmitter to transmit the detected signals generated according to the detected light. The system may further comprise a receiver to receive the detected signals transmitted by the transmitter, and a processor. The method may comprise comparing the detected signals with a predetermined threshold calculated from the transmission spectra of bile and of blood and determining the presence and/or concentration of bile and blood in-vivo.

23 Claims, 12 Drawing Sheets

(56) References Cited

U.S. PATENT DOCUMENTS

| | | | |
|---|---|---|---|
| 5,833,603 A * | 11/1998 | Kovacs et al. | 600/317 |
| 5,993,378 A | 11/1999 | Lemelson | |
| 6,240,312 B1 | 5/2001 | Alfano et al. | |
| 6,632,171 B2 | 10/2003 | Iddan et al. | |
| 6,689,056 B1 | 2/2004 | Kilcoyne et al. | |
| 6,884,213 B2 | 4/2005 | Raz et al. | |
| 7,468,044 B2 | 12/2008 | Iddan | |
| 7,684,840 B2 | 3/2010 | Palti | |
| 7,896,805 B2 | 3/2011 | Gilad et al. | |
| 7,901,366 B2 | 3/2011 | Iddan | |
| 7,938,775 B2 | 5/2011 | Rabinovitz | |
| 8,249,681 B2 | 8/2012 | Rabinovitz | |
| 8,290,556 B2 | 10/2012 | Rabinovitz | |
| 8,394,034 B2 | 3/2013 | Iddan | |
| 2002/0103417 A1 | 8/2002 | Gazdzinski | |
| 2004/0059204 A1 | 3/2004 | Marshall | |
| 2004/0181155 A1 | 9/2004 | Glukhovsky | |
| 2005/0137468 A1 | 6/2005 | Avron | |
| 2005/0272972 A1 | 12/2005 | Iddan | |
| 2006/0036166 A1 | 2/2006 | Horn | |
| 2006/0155174 A1 | 7/2006 | Davidson et al. | |
| 2006/0158512 A1 | 7/2006 | Iddan et al. | |
| 2006/0183976 A1 | 8/2006 | Adler et al. | |
| 2008/0064923 A1 | 3/2008 | Rabinovitz et al. | |
| 2008/0097182 A1 | 4/2008 | Schostek et al. | |
| 2008/0146896 A1 | 6/2008 | Rabinowitz | |
| 2008/0199065 A1 | 8/2008 | Swain | |
| 2009/0312631 A1 | 12/2009 | Rabinovitz | |
| 2011/0184293 A1 | 7/2011 | Rabinovitz | |

OTHER PUBLICATIONS

International Search Report for International Application No. PCT/IL2005/000525 dated Apr. 2, 2007.

Lewis B. "Capsule Endoscopy-Transit Abnormalities" GI Endoscopy Clinics of North America, Apr. 2006;16(2):221-8, vii.

Buscaglia et al. "Enhanced Diagnostic Yield with Prolonged Small Bowel Transit Time During Capsule Endoscopy" in International Journal of Medical Sciences, ISSN 1449-1907, 2008 5(6):303-308.

* cited by examiner

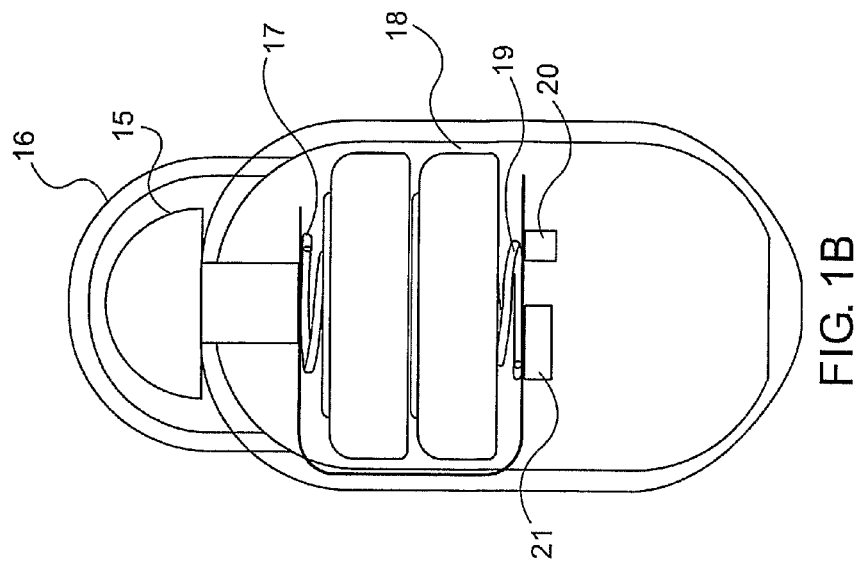
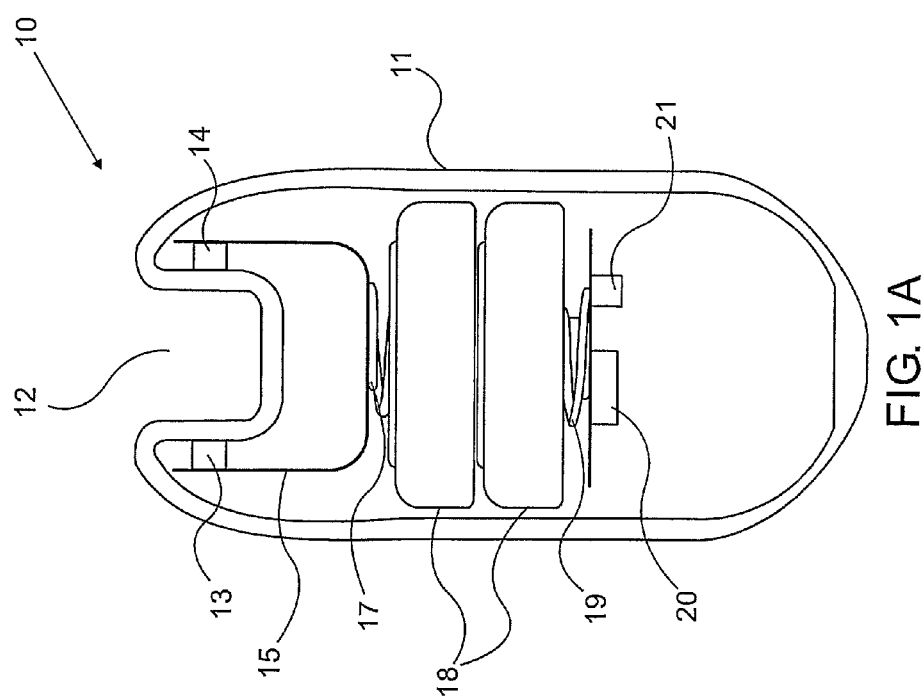

DEVICE, SYSTEM AND METHOD FOR DETECTION OF BLEEDING

CROSS-REFERENCE TO RELATED APPLICATIONS

This application is a National Phase Application of PCT International Application No. PCT/IL2010/000079, International Filing Date Jan. 31, 2010, which claims the benefit of U.S. Provisional Patent Application No. 61/148,319, filed Jan. 29, 2009, the contents of which are hereby incorporated by reference.

FIELD OF THE INVENTION

The present invention relates to the field of in-vivo detection. More specifically the present invention relates to a device, a system and method for the detection of bleeding in-vivo.

BACKGROUND OF THE INVENTION

In-vivo bleeding may occur due to different diseases in the body. Bleeding in the gastrointestinal (GI) tract may occur in various locations along the GI tract which may indicate different pathologies present at those locations. For example, bleeding in the esophagus may be due to esophagitis or due to ruptures in varices in the esophagus. An ulcer in the stomach, as well as an ulcer in the duodenum, may cause bleeding. And in the lower digestive tract, colorectal cancer may cause occult bleeding. Therefore, early detection of bleeding along the GI tract may be crucial for better treatment of many patients.

There are some known methods in detecting blood, such as using an endoscope to search for bleeding areas, which usually look for acute bleeding. Other methods may involve the use of dye or radioactive material swallowed by a patient such that the dye highlights blood vessels which are then imaged to detect bleeding. Another device which may be used is a device by NOVINEON HEALTHCARE TECHNOLOGY PARTNERS, GMBH, which may be fixed to the inner wall of a hollow organ and may provide continuous monitoring of bleedings. The device emits light having a predetermined wavelength and being at least partially absorbed or reflected in the interior of the hollow organ, and the device then detects the reflected light via a photosensitive sensor. Since blood has a characteristic absorption spectrum that differs from the absorption spectrum of the "normal" organ contents, it can be determined due to the detected reflections whether or not there is any blood inside the hollow organ.

However, this device doesn't take into consideration the presence of bile. Bile that is found in the small bowel may have transmission spectra that is similar to the transmission spectra of blood, such that there may be some inaccuracies regarding the determination of the presence of blood in-vivo. For example, if the transmission spectrum of bile is similar to the transmission spectra of blood, the device may give an indication as to the presence of blood, while there was actually bile present in the examined area. It is important to determine that the transmission spectra indicate the presence of blood and not the presence of bile.

SUMMARY OF THE INVENTION

Embodiments of the present invention provide a device, a system and method for the detection of in-vivo bleeding.

The device according to the present invention comprises a gap which is constantly in contact with in-vivo fluids, such that in-vivo fluids freely flow in and out of the gap. There may be several illumination sources, which may be positioned on one side of the gap, illuminating at different wavelengths, while on the opposite side of the gap there may be at least one light detector. The light detector is typically positioned such that it is facing the illumination sources, while the gap is placed in between the illumination sources and the light detector. Light illuminated by the illumination sources passes through the in-vivo fluids and onto the light detector. Some of the light may be absorbed by the in-vivo fluids, some may be reflected, and some may be transmitted to the light detector. The light detector may then transmit signals, created in response to the detected light, to an external receiver. A processor, external to the device, may process the signal sent by the light detector and create an absorption or transmission spectra of the in-vivo fluids. By comparing the signals to a reference transmission spectra of bile and to a reference transmission spectra of blood, it may be determined whether bile, blood or both are present in-vivo, and in what concentration, such that a conclusion may be made regarding presence of pathologies in-vivo. In other embodiments, instead of comparing transmission or absorption spectra, a comparison between discrete signals detected by the light detector and a predetermined threshold may be done.

The present invention overcomes the deficiencies of the prior art by being able to detect the presence of bile in-vivo, and thus determine whether the absorption or transmission spectra measured by the light detector indicates the presence of blood, the presence of bile or the presence of both. Furthermore, the system may determine the concentration of both bile and blood found in-vivo. In addition, in the present invention, the system may determine the location of the device in segment resolution. For example, the system may determine the location of the device along the GI tract segments, e.g., determine whether the device is in the esophagus, the stomach, the small bowel or the colon, based on the presence and/or concentration of bile. Other methods may be used to determine the location of the device in the different organs along the GI tract.

Some embodiments of the present invention describe other localization methods for determining where the in-vivo device is located in-vivo, e.g., along the GI tract. For example, the in-vivo device may include a pH detector which may continuously detect pH levels and may transmit the detected pH to a receiver external to a patient's body. Since, at different locations along the GI tract, there are different pH levels, the pH level detected may indicate on in-vivo location. Some methods may combine the two methods e.g., use detection of both the absorption or transmission spectra and the pH level.

Another device for locating the bleeding in-vivo may include one or more partitions within the gap. The partitions may divide the gap into several cells, such that each cell includes an illumination source and a light detector facing its corresponding illumination source. In other embodiments, a light beam illuminated by one illumination source is split by at least one partition into two or more beams crossing the gap. In such embodiments, the partitions may also divide the light detector corresponding to the divided light beam into two or more areas corresponding to the light paths of the divided beams. The path of each divided beam of light may be blocked by different enteric-coatings that coat the light detector(s) and/or fill each cell, such that only when the coating or filling is in contact with in-vivo conditions that cause the coating or filing to degrade would the divided light beam be able to cross the gap and reach its corresponding light detector, and only then would the in-vivo fluids absorption or transmission spectra be created. This ensures localization, since only at a specific location along the GI tract, for example, is the light path unblocked and may light pass through the fluids and be detected by the light detector. The in-vivo conditions that cause degradation of the different coatings may be pH, enzymatic activity, presence of bacteria, etc.

The present invention describes other devices which may also determine the location along the GI tract where the bleeding is present. Such devices may comprise a gap through which in-vivo fluids may pass in and out. These devices may include a substrate onto which binding agents are attached. The binding agents may bind to protein moieties of particles related with the presence of blood, for example, globin A and globin B, which are protein moiety of Hemoglobin, or the protein glycophorin A, which is one of the proteins located on the membrane of erythrocytes. Such proteins or protein moiety may bind to the binding agents attached onto the device, and may be illuminated and sensed by a light sensor such that there is an indication as to the presence of blood in-vivo. In order to locate where in-vivo the bleeding is located, the binding agent may be coated with different enteric-coatings that may degrade under different in-vivo conditions. For example, various pH levels, enzymatic activity, different bacteria, and/or other factors may lead to degradation of different enteric-coatings. The different enteric-coatings may be chosen such that each degrades at a different location along the GI tract and only then exposes the binding agents to the in-vivo fluids, which may or may not carry with it the proteins indicating bleeding.

BRIEF DESCRIPTION OF THE DRAWINGS

The present invention will be understood and appreciated more fully from the following detailed description taken in conjunction with the appended drawings in which:

FIG. 1A is a schematic illustration of a device for the detection of bleeding in-vivo in accordance with one embodiment of the invention;

FIG. 1B is a schematic illustration of a side-view of a device for the detection of bleeding in-vivo in accordance with one embodiment of the invention;

Figure 2:
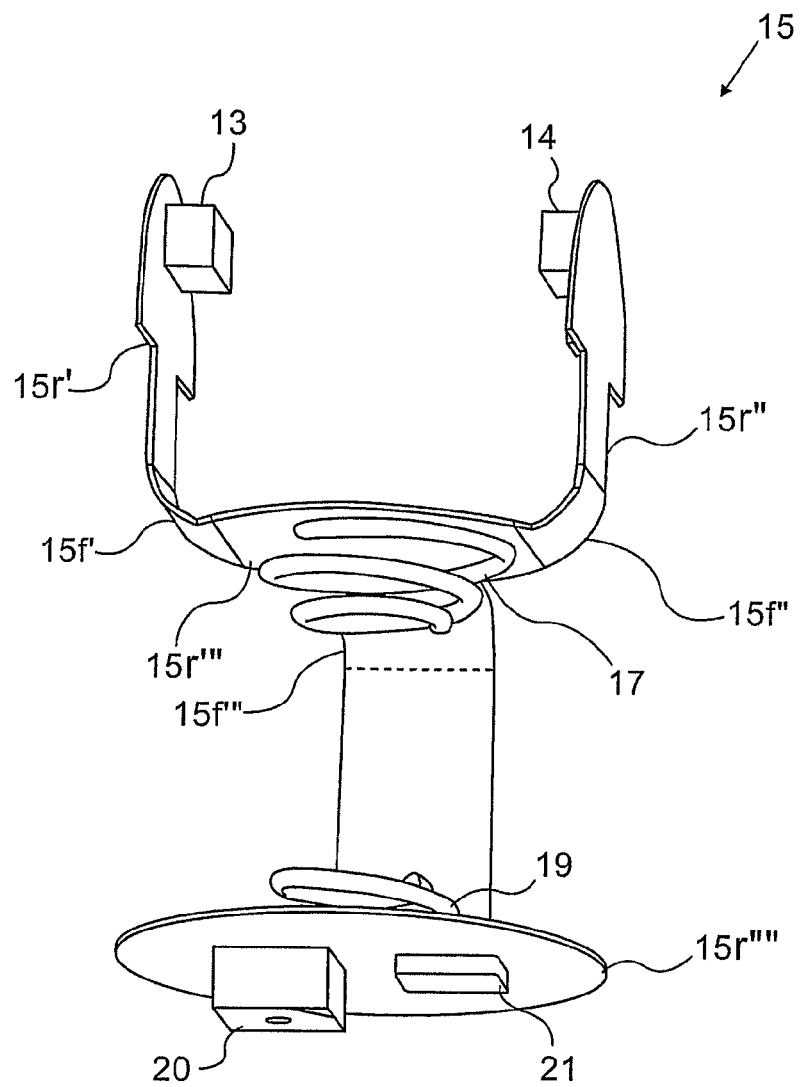
FIG. 2 is a schematic illustration of a printed circuit board assembly of a device for the detection of bleeding in-vivo in accordance with one embodiment of the present invention.

It will be appreciated that, for simplicity and clarity of illustration, elements shown in the figures have not necessarily been drawn accurately or to scale. For example, the dimensions of some of the elements may be exaggerated relative to other elements for clarity, or several physical components may be included in one functional block or element. Further, where considered appropriate, reference numerals may be repeated among the figures to indicate corresponding or analogous elements.

DETAILED DESCRIPTION OF THE INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as to not obscure the present invention.

Reference is now made to FIG. 1, which provides a schematic illustration of a device 10 for the detection of bleeding in-vivo. Embodiments of device 10 are typically autonomous, and are typically self-contained. For example, device 10 may be a capsule or other unit where all the components including, for example, power components are substantially contained within a housing or shell, and where device 10 does not require any wires or cables to, for example, receive power or transmit information. Device 10 may communicate with an external receiving and display system to provide display of data, control, or other functions. For example, in an autonomous system power, may be provided by an internal battery or a wireless receiving system. Other embodiments may have other configurations and capabilities. According to an embodiment of the invention, as described in FIG. 1, an in-vivo sensing device 10 may be administered in-vivo. Device 10 may be made of a biocompatible material such as polycarbonate, e.g., Isoplast® and Makrolon®. Other biocompatible materials may be used. Device 10 comprises device body 11 in which gap 12 is formed. Gap 12 may be hydro-dynamically curved to allow continuous flow of in-vivo fluids in and out of gap 12. In some embodiments, the width of gap 12 may be between 4-5 mm, although other widths may be used. In order for gap 12 to allow continuous flow of fluids in and out of it, the device 10 should constantly be in contact with in-vivo fluids. Therefore, in some embodiments, device 10 has a specific gravity of just above 1. When the specific gravity of device 10 is above 1, device 10 may pass through the colon in an optimal way. Specific gravity of just above 1 may ensure, on one hand, that device 10 does not float above the fluids, i.e., that device 10 and, more specifically, gap 12 is in contact with the fluids, and, on the other hand, may ensure that device 10 does not sink to the bottom of the lumen wall and lose the ability to move freely.

In some embodiments, in order to avoid entry of GI content other than fluids into gap 12, thereby perhaps blocking it, gap 12 may include a membrane cover, or a hydrogel cover, across the mouth of gap 12. The membrane or hydrogel may cover the entire gap 12, and may have holes or pores that allow only particles of a certain size or smaller to pass through them. The size of the pores in the membrane or hydrogel may be designed to allow passage of particles with a size similar to the size of blood particles flowing in in-vivo fluids. For example, the size of the pores may be similar to the sizes of globin A and globin B or of glycophorin A.

On one side of gap 12 there may be an illumination source 13, such as an LED or a Vertical-cavity surface-emitting laser (VCSEL), and on the opposite side of the gap 12 there may be a light detector or photo detector 14. Illumination source 13 may be an LED such as Hyper TOPLED® by Osram™ and KPHHS-1005SYCK® by Kingbright™, though other illumination sources may be used. Light detector or photodiode 14 may be, for example, opt101® by Burr-Brown Products™ from Texas Instruments, mlx75305C® by Melexis™ Microelectronic Integrated Systems, or tsl12s-e23® by TAOS™ (Texas Advanced Optoelectronic Solutions). other photodiodes may be used. Light detector 14 is positioned such that it is directly facing the illumination source 13, while gap 12 is located between the illumination source 13 and the light or photo detector 14. Illumination source 13 may illuminate the in-vivo fluids which freely flow through gap 12, and the light passing through the fluids (whether some of the light was absorbed by particles in the fluid, or whether some of it was reflected from the flowing particles) may then be detected by light detector 14. According to some embodiments, the illumination source 13 may illuminate at a low frequency in order to save energy during the procedure of blood detection. Detector 14 may also be activated in synchronization with the illumination source 13, e.g., illumination source 13 and light detector 14 may detect signals every 10 sec or every 1 minute. Other frequencies may be used.

Device 10 may further comprise a printed circuit board assembly (PCA) 15 onto which illumination source 13 and light detector 14 are electronically connected. The PCA 15 may be made of rigid portions and flexible portions. Onto PCA 15 may further be mounted a transmitter 20 and antenna 21. The light detector 14 may pass to the transmitter a signal created by the detected light, which had passed through the in-vivo fluids. In order to preserve energy, transmitter 20 may be synchronized with the light detector 14. Device 10 may further comprise batteries 18, such as silver-oxide batteries, and battery contacts 17 and 19 which are both mounted on PCA 15. Batteries 18 should supply enough power to keep device 10 operating during its passage through the entire GI tract, e.g., at least for as long as 72 hours.

Illumination source 13 may include several, for example, at least four, white LEDs with different filters for illuminating at a specific narrow wavelength, or may include several, for example, at least four, different VCSEL illuminating at different specific wavelengths. Illumination source 13 may typically comprise at least four illumination sources which may illuminate at different narrow band illumination, e.g., at 560 nm, 610 nm, 700 nm, and 800 nm (as will be explained in detail with reference to FIGS. 11-12). The illumination sources 13 may operate in an alternating or sequential mode with different pulse duration, in order to distinguish between the different illumination sources being constantly detected by the light detector 14. For example, one illumination source 13 may illuminate the in-vivo fluids for a certain predetermined time period and then stop, and a second illumination source may begin illuminating the in-vivo fluids for another time period. When the second illumination source stops illuminating, the third illumination source may begin illuminating for yet another predetermined time period. When the third illumination source stops its operation, the fourth illumination source may begin to operate. Once the fourth illumination source has ceased its operation, the first illumination source may begin illuminating again, and so on. In some embodiments, the predetermined duration of illumination may differ for each illumination source, but in other embodiments, they may all illuminate for the same duration, one subsequent to the other. The light detector 14 may then detect light, which passes through the in-vivo fluids, from one of the four illumination sources 13 at a time.

According to other embodiments, there may be a white light broad band illumination source 13, and light detector 14 may comprise at least four light detectors. Each light detector 14 may comprise a different filter for collecting light at a different wavelength, after passing through the in-vivo fluids. The filters may be narrow band filters, interference filters or diffractive optical element (DOE) filters.

While or after the device 10 passes through the GI tract, the signals detected by light detector 14 are transmitted by a transmitter 20 to an external receiver, outside the patient's body (not shown). The receiver may include a processor which may create transmission spectra of the in-vivo fluids according to the signals detected from the at least four wavelengths. The processor may further compare the transmission spectra of the in-vivo fluids to a reference transmission spectra of bile and to a reference transmission spectra of blood (shown in FIG. 11), which are created by detecting transmission spectra of bile and of blood in water and of different concentrations of bile vs. blood, and thus determine whether there is bile in-vivo, whether there is blood in-vivo or whether there is both. Furthermore, the processor may compare between the measured transmission spectra with the reference spectra and may determine the concentration of either bile, blood or both. When there is both bile and blood present, the processor, by comparing the measured transmission spectra to the reference spectra, may indicate whether the ratios between the bile and the blood indicate bleeding or whether the results indicate high concentration of blood but with no real bleeding, which may also indicate a pathology. In other embodiments, the concentration of blood, along with other detected in-vivo data, may indicate the location of the blood in-vivo. In other embodiments, instead of comparing between transmission or absorption spectra, a comparison between discrete signals detected by the light detector and a predetermined threshold may be done, as will be described in detail below, with reference to FIGS. 11-12.

In other embodiments, there may be several, for example, at least four, illumination sources 13, each illuminating at different narrow band illumination, while there may be a corresponding number of light detectors 14. Each of the four light detectors 14 may be positioned such that it is facing its corresponding illumination source 13, with a respective gap 12 in between. In order to ensure that light from one illumination source 13 would not be detected by a non-corresponding light detector 14, the light may first pass through a collimator and only then pass through the in-vivo fluids. Each narrow band illumination source 13 may comprise a collimator that may collimate the light before it passes through the fluids and reaches its corresponding light detector 14, which is positioned on the opposite side of the gap, facing the illumination source. Another way to achieve correlation between a light detector and an illumination source is by placing different filters onto the light detectors such that each light detector 14 may detect light at a specific, and perhaps different, wavelength. The filters may be narrow band filters, interference filters or diffractive optical element (DOE) filters.

According to some embodiments, device 10 may comprise a pH detector (not shown). An example for a pH detector may be the pH detector by Endonetics Inc. as disclosed in U.S. Pat. No. 6,689,056. Such a pH detector may continuously detect pH levels, and transmitter 20 may transmit the detected pH along with the signals detected by light detector 14 to a receiver external to a patient's body. Since, at different locations along the GI tract there are substantially different pH levels, the detected pH may indicate the in-vivo location. For example, in the stomach there is a low acidic pH of between 1 to 4, while in the small bowel the pH values are between 7 to 8 (slightly alkaline), and in the colon the pH is between 5.5 and 7 (slightly acidic).

In other embodiments, the in-vivo location where blood is detected may be calculated by an algorithm, such as disclosed in U.S. Pat. Nos. 7,596,403. 7,596,403 discloses a method for determining path length through a body lumen, for example, path length or distance to a specified location. This information may be used alone or in combination with other in-vivo data, such as pH, in order to determine the in-vivo location in which light detector 14 detects light signals, which may indicate on the presence of blood.

Device 10 may be a swallowable capsule. Typically, device 10 is inserted into the GI tract of a patient by swallowing it. Other ways of insertion of device 10 may be used, e.g., by a capsule delivery device such as the one disclosed in U.S. Pat. Nos. 6,632,171 and 6,884,213, or by surgery. Device 10 may pass along the GI tract through natural peristalsis movements.

Reference is now made to FIG. 1B which is a schematic illustration of a side-view of a device for the detection of bleeding in-vivo in accordance with one embodiment of the invention. FIG. 1B is a schematic illustration of a side-view of device 10, which is shown in FIG. 1A. FIG. 1B depicts the side of device 10 mainly describing the shape of the rigid portion of the PCA 15, onto which the illumination source 13 is mounted. That same shape of a rigid portion of PCA 15 is used to mount the light detector 14 opposite the illumination source 13 so that light detector 14 directly faces illumination source 13. In this embodiment, the shape of the rigid portion of PCA 15 onto which illumination source 13 is mounted is shown to be a half circle. However, other shapes may be used, as long as they comply with the shape and size of both sides of device 10, on either side of gap 12. Typically, the finish of device 10 should be round with no sharp edges, so that it is suitable for in-vivo insertion either by swallowing or through other methods, such that it would not cause any damage to tissue during insertion. Furthermore, device 10 should be designed with rounded edges so it does not cause any harm to tissue while passing along the GI tract by natural peristalsis. Therefore, the shape of a half of a circle for the rigid potion of the PCA 15 to which illumination source 13 and light detector 14 are connected, may be suitable. In other embodiments, other shapes such as a triangle, rectangle, and square may be used for the PCA 15, as long as the shape of the shell or housing 16 of device 10 covering the PCA 15, is not sharp and is suitable for insertion in-vivo, since that is the part that actually comes in contact with in-vivo tissue. For example, the shell or housing 16 of the housing of device 10 that covers the PCA 15 may be a rounded half of a circle, no matter what shape PCA 15 is. Part 16 is typically a transparent window with rounded edges.

Reference is now made to FIG. 2 which is a schematic illustration of a printed circuit board assembly (PCA) of a device for the detection of bleeding in-vivo in accordance with one embodiment of the present invention. According to an embodiment of the invention, as shown in FIG. 2, there is provided a printed circuit board assembly (PCA) 15. PCA 15 may comprise rigid portions 15*r* and flexible portions 15*f*.

As described in FIG. 1B above, in one embodiment, two of the rigid portions 15*r'* and 15*r"* onto which illumination source 13 and light detector 14 are respectively mounted, are in the shape of a half a circle. However, other shapes may be used. The PCA 15 may be designed such that at the end of each rigid portions 15*r* is a flexible portion 15*f*. Flexible portions 15*f'* and 15*f"* may be folded in order to adjust the shape of the PCA 15 to fit within the volume of device 10. For example, flexible portions 15*f'* and 15" are each connected on one end to the ends of two rigid portions 15*r'* and 15*r"'*, respectively, and on the other end, to one mutual rigid portion 15*r"'*. The flexible portions 15*f'* and 15*f"* are then folded to create a U shape which fits the U shape of device 10, designed such that there is room between rigid portions 15*r'* and 15*r"* for gap 12.

Another rigid portion 15*r""* may be connected through a flexible portion 15*f"'* to the rigid portion 15*r"'* located at the bottom part of the U shaped PCA 15. Connected to the rigid portion 15*r"'* may be battery contacts 17 and facing battery contacts 17 may be battery contacts 19, which are connected to rigid portion 15*r""*. In between battery contacts 17 and 19, batteries 18 may be inserted (as shown in FIGS. 1A-1B). Furthermore, the PCA 15 may comprise a transmitter 20 and an antenna 21 which may transmit the signals detected by the light detector 14 to an external receiver (shown in FIG. 3) by wireless communication, e.g., RF transmission. Other methods of transmission may be used. Transmitter 20 may include control capabilities, for example, for controlling the various operations of device 10, although control capabilities or one or more aspects of control may be included in a separate component. Transmitter 20 is typically part of an ASIC (application specific integrated circuit), but may be of other constructions; for example, transmitter 20 may be a processor executing instructions. Device 10 may include a processing unit separate from transmitter 20 that may, for example, contain or process instructions.

Figure 3:
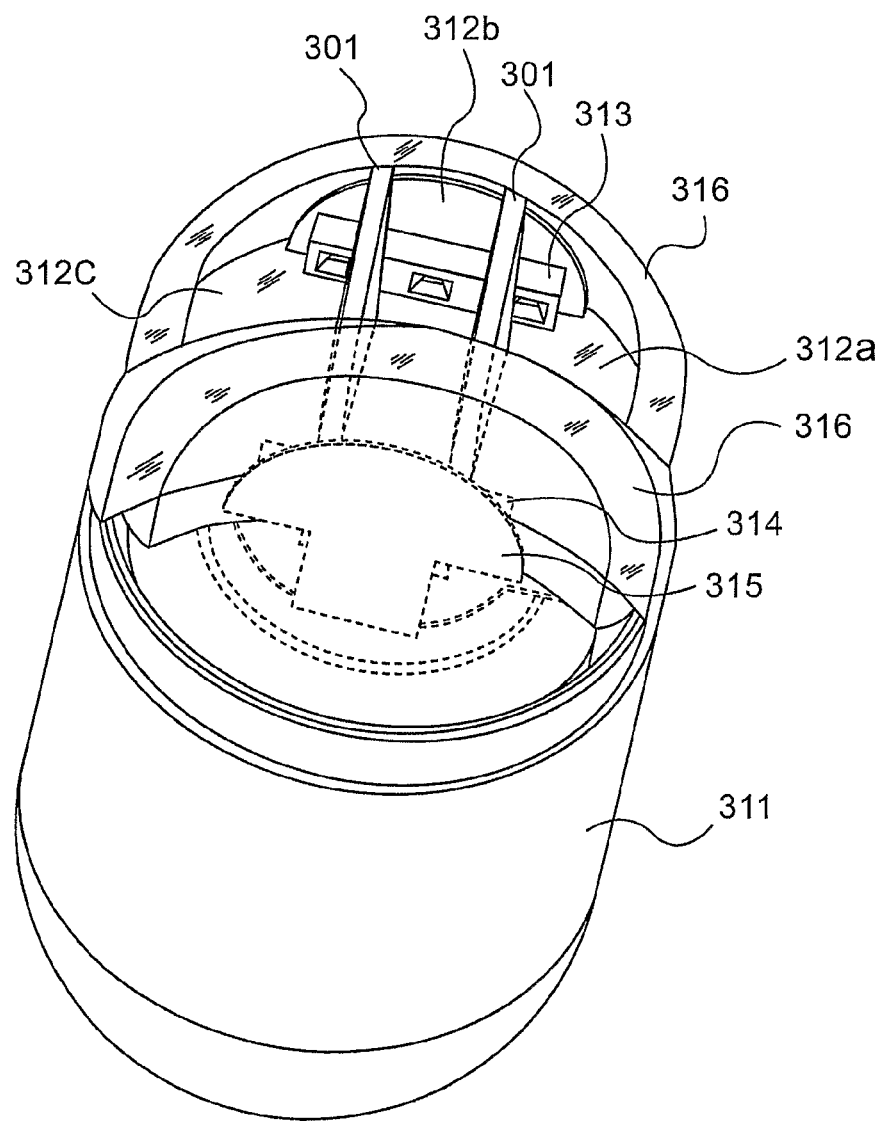
FIG. 3 is a schematic illustration of a device for the detection of bleeding in-vivo in accordance with another embodiment of the present invention.

Reference is now made to FIG. 3, which is a schematic illustration of a device for the detection of in-vivo bleeding in accordance with another embodiment of the present invention. According to embodiments of the present invention, as shown in FIG. 3, a device 300, which may be similar to device 10 as described in FIGS. 1A-1B, may comprise a device body or shell 311 which may contain illumination source 313 and light detector 314 mounted on a PCA 315.

However, unlike device 10, device 300 has an additional feature of one or more partitions 301 placed across the gap 312 between illumination source 313 and light detector 314 such that more than one cell is created, for example, cells 312*a*, 312*b* and 312*c*. Partitions 301 create the plurality of cells 312*a*-*c*, while ensuring that each cell has its own illumination source 313 and its own light detector 314, which are positioned one opposite the other in each cell. Typically, each illumination source 313 and its corresponding light detector 314 are facing one another. Each of cells 312*a*-*c* may be in contact with in-vivo fluids.

In order to detect bleeding in-vivo and, in addition, to determine the location of the bleeding along the GI tract, the cells 312*a*-*c* may be filled and/or coated with a different enteric-coating material. Each cell may be designed to open (i.e., the enteric-coating material covering and/or filling the cell is designed to degrade) and thus enable light to pass from illumination source 313 through the in-vivo fluids which freely pass in and out of the cell and onto light detector 314, at a different location along the GI tract. For example, before device 300 is inserted in-vivo (e.g., by swallowing device 300), all of cells 312a-312c are filled and coated with specific enteric materials. When the device 300 reaches the esophagus and the stomach, for example, cell 312a which is filled with a filler designed to degrade when in the environment of the stomach (e.g. gelatin), opens. When the filler in cell 312a degrades, in-vivo fluids from the stomach may flow in and out of cell 312a. Light from illumination source 313 may now reach light detector 314 which was until now blocked by the filling and/or coating of cell 312a. The light detector 314, which is within cell 312a, may detect light signals and may transmit them to an external receiver through a transmitter, e.g., transmitter 20 as in device 10. In other embodiments, the cell 312a, which is designed to detect blood in the stomach, may not be coated at all, since the stomach is practically the first organ through which the device passes in its travels through the GI tract.

When the device 300 continues along the GI tract, it reaches the small bowel. Cell 312b, for example, may be coated and filled with a material that withstands the low pH present in the gastric juice (e.g., pH around 3), but that may degrade in a higher pH (e.g., pH above 5.5), thus emptying cell 312b of its content. When cell 312b is free of the material filling it, in-vivo fluids of the small bowel may now enter and exit freely through cell 312b, thus enabling light to pass through the in-vivo fluids from illumination source 313 and onto light detector 314, within cell 312b. Other small bowel specific materials may be used, such as, for example, time dependent materials that are designed to degrade after a predetermined time period that corresponds to the known approximate transit time of the device 300 in the stomach, until it reaches the small bowel. The typical transit time of an in-vivo device in the stomach is between a few minutes to one hour. (see, "Capsule endoscopy-Transit abnormalities" by Lewis B. in *GI Endoscopy Clinics of North America*). Further examples for materials which may be used may depend on enzymatic reactions which are small intestine dependent, etc.

The device may further pass along the GI tract and reach the colon. When the device reaches the colon, the material filling cell 312c, which may be comprised of material that is designed specifically to degrade in colon fluids, may degrade, such that light from illumination source 313 within cell 312c, may pass through colon fluids and onto light detector 314 within cell 312c. The light detector 314 of cell 312c may then detect light signals of the colon fluids and thus detect bleeding. The degrading of the material filling cell 312c may be pH dependent. Examples for pH dependent fillings, which degrade only in a pH above 5.5 may be made of methacrylic acid copolymers, e.g., Eudragit® polymers, which have a variety of grades such that each type of Eudragit® polymers degrade at different pH level. Other enteric polymers may include polyvinyl acetate phthalate, hydroproxypropyl methylcellulose phthalate, cellulose acetate phthalate, and cellulose acetate trimelliate, or a combination thereof. These polymers may be made as matrices for filling the cells.

Other filling (and coating) materials dedicated to degrading in the colon may be polymers which degrade in the presence of colon bacteria or due to enzymatic reaction which is colon specific. For example, biodegradable polymers or azo polymers in matrices configurations may be used as fillers (or in coatings), since they degrade by the azoreductase enzymes produced by the azobacters present in the colon. Other colon specific materials may be made of polysaccharides matrices which remain in tact in the stomach and small bowel but in the colon are degraded by bacterial polysacharidases. For example, amylase, guar gum, pectin, chitosan, inulin, cyclodextrines, chondroitin sulphate, dextrans and locust bean gum.

Other materials may be time dependent, such that they are designed to degrade after a predetermined time period which corresponds to the known approximate transit time of the device 300 in the small bowel, until it reaches the colon. The typical transit time of an in-vivo device in the small bowel, without in taking any boosts, is 2-8 hours (see, "Enhanced Diagnostic Yield with Prolonged Small Bowel Transit Time During Capsule Endoscopy" by Buscaglia et al. in *International Journal of Medical Sciences*). Therefore, a filling or coating material occupying cell 312c, for example, which is dedicated to degrade in the colon, may be designed to degrade after 6 hours from the time device 300 is swallowed. Six hours may be the sum of an approximate transit time of the 1 hour that it would take device 300 to pass through the stomach and the approximate transit time of 5 hours that it would take device 300 to pass through the small bowel. The transit time of device 300 in the small bowel, until it reaches the colon, may be controlled and shortened by performing the procedure of inserting the device 300 into the GI tract, along with in taking laxatives and boosters. If the procedure of inserting device 300 (or 10) and determining the presence of blood is to be done in a substantially short time, a patient may be instructed to take a boost at a specific time before and/or after inserting the device 300, e.g., eating a large meal at a specific time-line. Other methods may include in taking laxatives in order to shorten the procedure time.

The illumination source 313 in each cell of cells 312a-312c may comprise more than one illumination source, for example three or four illumination sources. Accordingly, there may be a corresponding number of light detectors 314 in each cell. Each of the plurality of light detectors 314 in each cell may comprise different filters, such that specific wavelengths of light passing through the in-vivo fluids in every specific location along the GI tract may be detected by a corresponding light detector. The signals detected by the light detectors in each cell may be used for comparing the signals at specific wavelengths to a reference transmission spectrum of bile and blood, such that a conclusion on the presence of bile, blood or both may be made.

In other embodiments, there may be a plurality of separate gaps, each positioned along the circumference of device 300 but at a different side. Each gap may be positioned on the circumference of the device; such that it may be in contact with in-vivo fluids. The gaps may be located on different sides of device 300. Each gap may comprise a plurality of illumination sources each illuminating at a different wavelength and a light detector for detecting the light signals emitted by the in-vivo fluids flowing in and out of each gap. In some embodiments, each gap may be coated/filled with a different coating/filling designed to open or degrade at a different location along the GI tract, as discussed above.

In other embodiments, there may be one gap comprising a plurality of illumination sources illuminating at specific wavelengths and a light detector. In another side along the circumference of device 300, there may be cells or chambers with different coatings designed to open at a different location along the GI tract. Each of these chambers may comprise a photo detector which may detect whether the chambers have opened or are still closed. The chambers may also include a small light source, such that if the photo detector in a chamber detects a dark image, it can be inferred that the chamber is still closed, whereas when the photo detector detects a bright image, it can be inferred that the chamber is open, i.e., that the coating and/or filling occupying the chamber have degraded. A combination of the information from the light detector within the gap along with the image of the chamber may indicate on the presence of blood in-vivo along with the location in-vivo.

Figure 4:
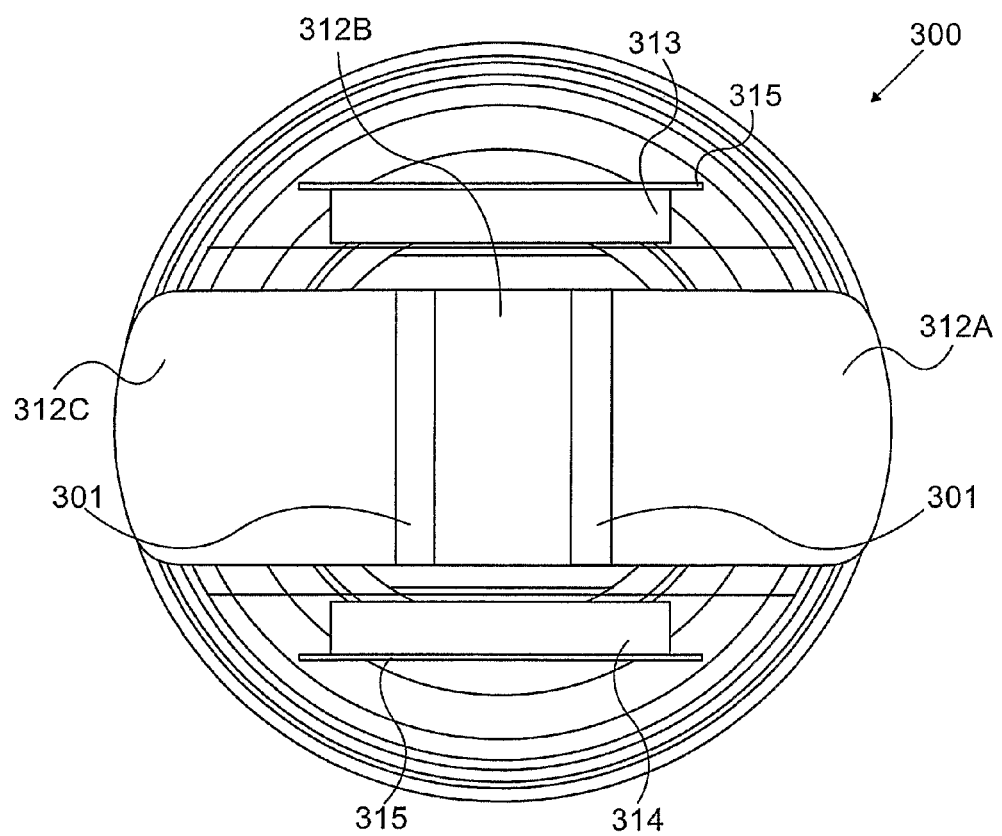
FIG. 4 is a schematic illustration of an upper view of a device for the detection of bleeding in-vivo according to another embodiment of the present invention.

Reference is now made to FIG. 4, which is a schematic illustration of a top view of a device 300 for the detection of bleeding in-vivo according to the embodiment of FIG. 3 as well as another embodiment of the present invention, showing the closed cells 312a-c. According to some embodiments, partitions 301 may be opaque such that illumination from one cell would not reach a neighbor cell. In some embodiments, illumination source 313 may be positioned on PCA 315 such that illumination from illumination source 313 would reach each of the cells 312a-312c. For example, the illumination source 313 may be divided into a plurality of illumination sources so that each cell 312a-312c may have one or more illumination sources illuminating it.

Accordingly, light detector 314 may be positioned on PCA 315 such that light signals of light passing through in-vivo fluids would be detected in each of the cells 312a-312c. For example, the light detector 314 may be divided into a plurality of light detectors so that each cell 312a-312c may have one or more light detectors, perhaps corresponding in number to the number of illumination sources illuminating at different wavelengths. According to other embodiments, device 300 may comprise one illumination source for each of cells 312a-312c which would illuminate in white broad band illumination, while each cell may have a plurality of light detectors, each detecting light signals at a different specific wavelength or wavelength ranges. The plurality of light detectors, typically between three to four light detectors, may comprise filters so that they may detect light of a specific wavelength. Such filters may be narrow band filters, interference filters or diffractive optical element (DOE) filters.

Illumination sources 313 may continuously illuminate each of the cells 312 not being dependent on the operation of light detectors 314. In some embodiments, when a cell, for example cell 312b, is still filled with an enteric material, light from illumination source 313 cannot reach light detector 314 within cell 312b. A processor, within device 300 or external to the device 300, may control the illumination pulse duration such that when the light detector 314 detects no signals, the illumination source 313 is adjusted to illuminate at a low frame rate or may be adjusted to illuminate for only short periods with long durations between each period. In the same way, the light detector 314 in cell 312b may be adjusted to detect light signals at a low frame rate, in order to better conserve power of device 300 ("sleep mode"). However, when the filler in cell 312b is degraded, the light detector 314 in cell 312b begins to detect light signals. This is when the processor may control the illumination source 313 and light detector 314 (or only one of them) to illuminate at a high rate and to detect light signals at a high frequency, respectively ("awake mode").

In some embodiments, instead of device 300 comprising partitions 301 for creating different cells 312a-312c that open at different locations along the GI tract, device 300 may comprise a pH detector (not shown). A pH detector may continuously detect pH levels and may transmit the detected pH to a receiver external to a patient's body. Since there are different pH levels at different locations along the GI tract, the pH detected may indicate a specific in-vivo location. According to other embodiments, the pH detector may be an additional sensor in addition to the plurality of cells 312a-312c.

In some embodiments, device 300 may further comprise a counter which may assist in indicating the time passing from insertion of the device into the body lumen. Such a counter may give a rough estimation as to the location in-vivo, e.g., along the GI tract. That is, the time from insertion of the device until reaching certain organs along the GI tract may either be known based on statistics (e.g., studies on peristaltic movement duration) or may be on a predetermined time-line when the procedure of insertion of the device includes taking boosters and laxatives.

Figure 5:
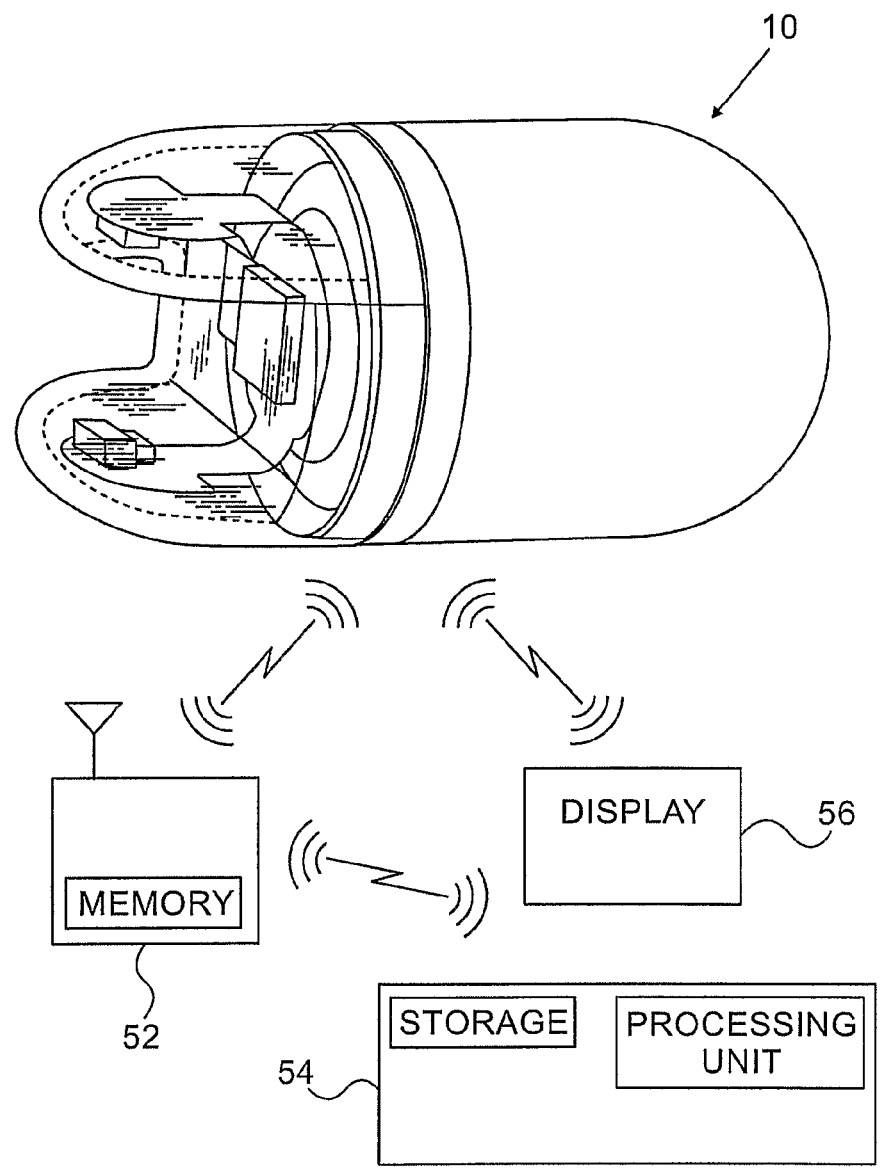
FIG. 5 is a schematic illustration of a system for the detection of bleeding in-vivo in accordance with one embodiment of the present invention.

Reference is now made to FIG. 5, which is a schematic illustration of a system for the detection of bleeding in-vivo in accordance with one embodiment of the present invention. Device 10 may comprise a transmitter 20 as shown in FIG. 2. Device 10 or device 300 may transmit the detected illumination which passed through the in-vivo fluids, to an external receiver 52. Receiver 52 may comprise a memory unit for storing the data transmitted from device 10 or device 300.

A system according to some embodiments of the invention includes an in-vivo sensing device transmitting light signal and/or other information (e.g., images, pH values etc.) to a data receiver and/or recorder 52 possibly close to or worn on a subject. A data receiver and/or recorder 52 may of course take other suitable configurations. The data receiver and/or recorder 52 may transfer the received information to a larger computing device 54, such as a workstation or personal computer, where the data may be further analyzed, stored, and/or displayed to a user. In other embodiments, the display 56 may be a separate unit not part of the computing device 54. In other embodiments, each of the various components need not be required; for example, an internal device may transmit or otherwise transfer (e.g., by wire) information directly to a viewing or processing system.

In some embodiments, computing device 54 may comprise a processing unit and a storage unit. The processing unit may create a transmission spectrum from the light signals detected by the light detector 14 (or 314) which correspond to the transmission spectra of the in-vivo fluids. The processing unit may then compare the created transmission spectra to reference transmission spectra of, e.g., bile. The processing unit may either compare the entire spectra or compare only a number of values in order to determine whether bile is present in the correlating locations in-vivo. For example, illumination sources 13 and 313 may illuminate in the wavelengths of around 500 nm, 700 nm and 850 nm. The ratio of transmission of bile between a wavelength of 450 nm and 700 nm is very high (around 1000) which is similar to how the transmission spectrum of blood behaves. Therefore, in order to determine whether bile is present in-vivo at a specific location, there is a need for a calculation of an additional ratio which would give a result unique to the transmission spectrum of bile and not of blood. For example, the ratio between wavelengths of 700 nm and 850 nm is calculated in that location. This ratio between 700 nm and 850 nm is then compared to a reference value which may be calculated from the transmission spectrum of bile in water, and may indicate the presence of bile. The ratio between 700 nm and 850 nm in bile is typically larger than that ratio in blood; therefore this ratio is suitable to indicate the difference between the two. If the ratio calculated from in-vivo signals exceeds a certain threshold calculated by the processor from the reference spectra, it may be an indication to the presence of bile in-vivo in that specific location where the ratio between 700 nm and 850 nm was calculated.

In order to determine the presence of blood in-vivo, an additional ratio should be calculated and compared to a reference. For example, the ratio of transmission between a wavelength of 576 nm and 700 nm is calculated. The ratio is then compared to a reference value which may be calculated from the transmission spectrum of blood in water. If the ratio calculated from the detected signals exceeds a certain threshold calculated based on the reference transmission spectrum of blood, this may indicate to the presence of blood which may indicate a pathology in-vivo.

Therefore, in order to determine the presence of blood in-vivo and or the presence of bile, the illumination sources 13 or 313 may typically illuminate in three different wavelengths, e.g.: 576 nm, 700 nm and 850 nm. Other options may include wavelengths of: 415 nm, 540 nm, 560 nm, 700 nm and 850 nm. Typically, a certain wavelength would be used in all of the ratios. This wavelength should be one that experiences good transmission in blood, e.g., 700 nm.

Furthermore, there may be an indication as to whether or not the blood is oxygenated. In the transmission spectrum of blood in water, there are two minimum peaks, one around the wavelength of 542 nm and one around 576 nm. These peaks are an indication of the presence of oxygenated blood. If, in the transmission spectrum created by the detected signals, there are no peaks around the wavelength of 542 nm and around 576 nm, then this may be an indication that the blood is not oxygenated. Therefore, if device 10 or 300 comprises five illumination sources with five different wavelengths, the processor may indicate the presence of bile, the presence of blood and whether or not the blood is oxygenated. For example, the five wavelengths may be 415 nm, 542 nm, 576 nm, 700 nm, and, 850 nm.

In some embodiments, display 56 may display the transmission spectra of the in-vivo fluids. In other embodiments, the display 56 may display the transmission spectra along with other information, e.g., pH values at the correlating in-vivo locations of where the light signals are detected. In other embodiments, where device 10 may for example comprise an imager and a broad band illumination, i.e., white light, in-vivo images may be displayed either alone or alongside the in-vivo locations where blood/bile or both are detected.

According to some embodiments, receiver 52 may be a disposable receiver. In some embodiments, the receiver may be a wearable disposable patch. A patient may wear the receiver and may swallow a new device 10 or 300 every day for a week, for example, in order to monitor the in-vivo environment to detect bleeding. This is because bleeding may not always be a constant pathology, but rather bleeding may be active on one day, may stop for a day or two, and may be noticed again on a different day. Therefore, there may be a need to monitor the bleeding during a long period of time, e.g., a week, by inserting into a patient a new device every day over the course of a week. The receiver may include a visual indication, which may show where along the GI tract blood was detected. For example, the receiver may include different LEDs corresponding to various locations along the GI tract, e.g., esophagus, stomach, small bowel and colon. The LEDs may light up when a detection of bleeding is made by the light detector (14 or 314). For example, if blood if detected in the small bowel, the LED corresponding to the small bowel may light up indicating to the patient and/or the physician the patient's condition.

In other embodiments, there may be other methods of indicating to the patient and his physician the patient's condition. In yet other embodiments, the indication may be encoded so that the patient's medical condition would not be clear to the patient, but rather the physician alone would know how to read the indication. This may be useful in avoiding the patient from being anxious and worried if he would be able to see and understand the results of the procedure.

Figure 6:
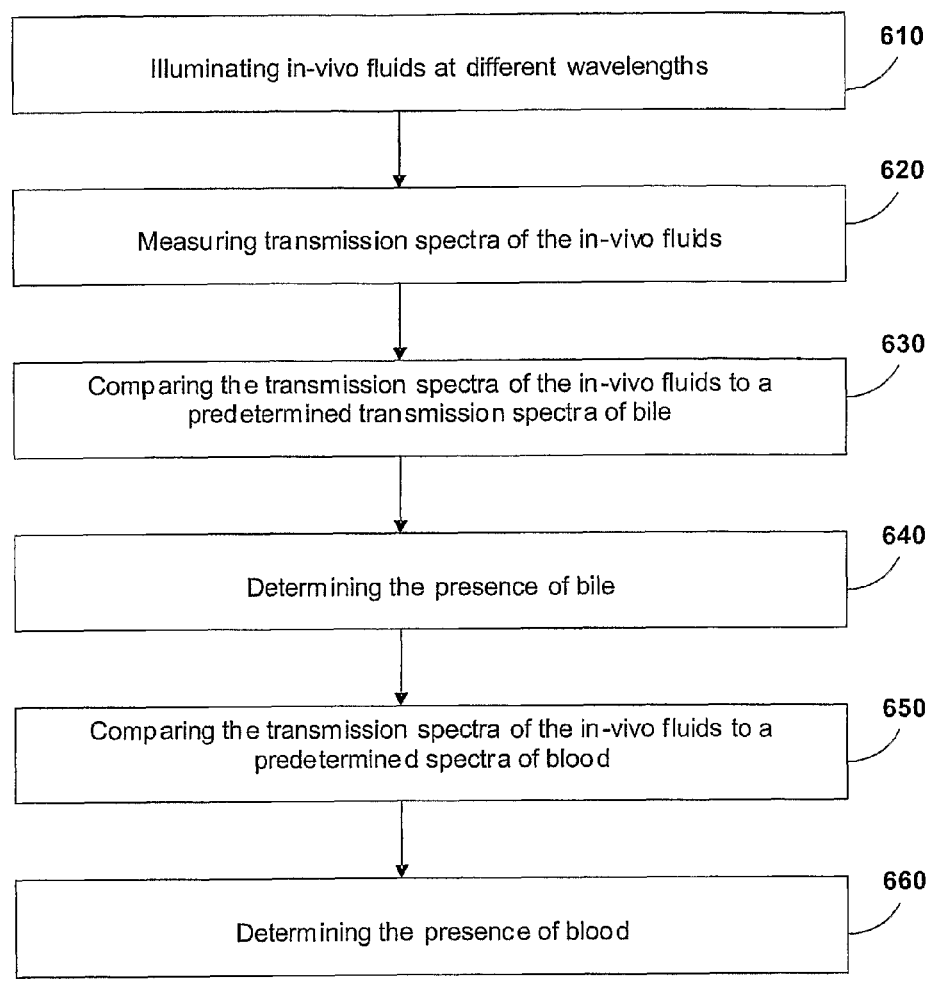
FIG. 6 depicts a method for the detection of bleeding in-vivo according to one embodiment of the present invention.

Reference is now made to FIG. 6 which depicts a method for the detection of bleeding in-vivo according to one embodiment of the present invention. The method according to FIG. 6 may comprise illuminating in-vivo fluids at different wavelengths (610) and measuring transmission spectra of the in-vivo fluids (620). The method may further comprise comparing the transmission spectra of the in-vivo fluids to a predetermined transmission spectrum of bile in a specific wavelength (630), which may be done either by a processor within the device 10 or 300 or by a processor external to the device 10 or 300. The comparison between the spectra may result in determining the presence of bile in that specific location in-vivo (640). The method may comprise comparing the transmission spectra of the in-vivo fluids to a predetermined spectrum of blood in a specific wavelength (650) and thereby determining the presence of blood according to the transmission spectra (660). In other embodiments, instead of comparing between transmission or absorption spectra, the method may comprise comparing between discrete signals detected by the light detector and a predetermined threshold, as will be described in detail below, with reference to FIGS. 11-12.

Figure 7:
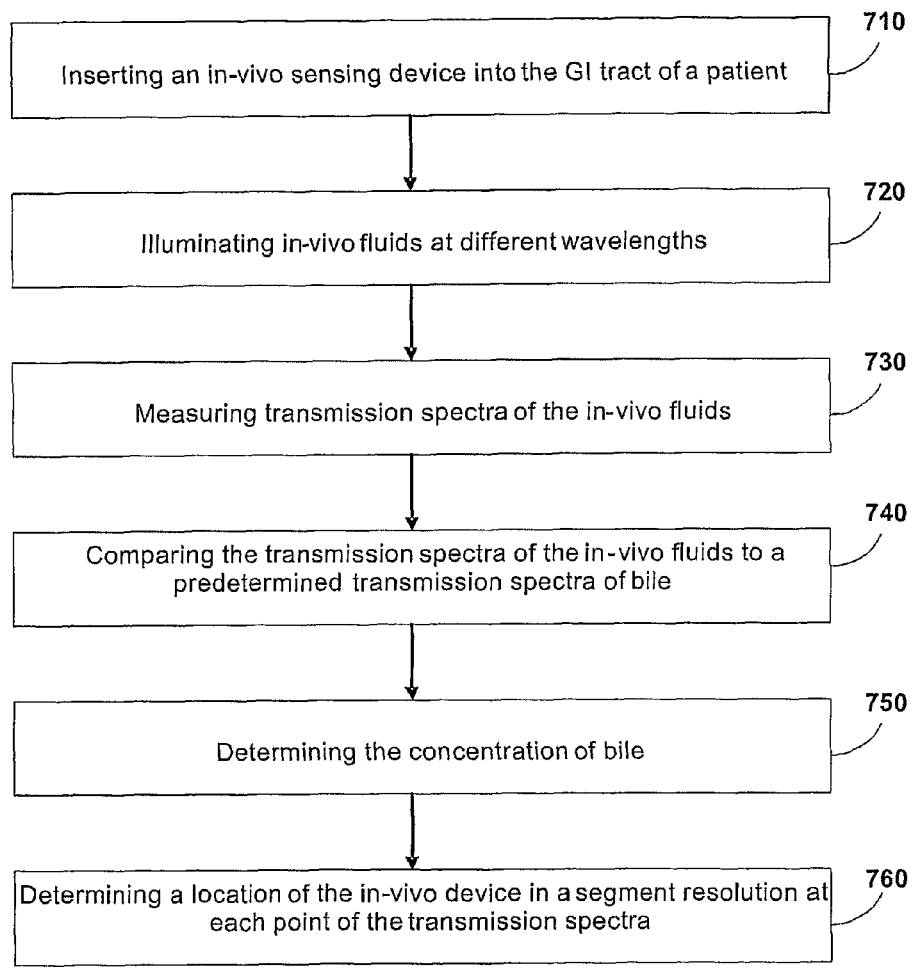
FIG. 7 depicts a method for the detection of bleeding in-vivo according to another embodiment of the present invention.

Reference is now made to FIG. 7 which depicts a method for the detection of bleeding in-vivo according to another embodiment of the present invention. The method according to FIG. 7 may be a method for localizing an in-vivo sensing device in segment resolution along the gastrointestinal (GI) tract and detecting the presence of blood at each location. The method may comprise inserting an in-vivo sensing device into the GI tract of a patient (710). According to embodiments of the invention, the device may comprise a gap through which in-vivo fluids flow in and out, one or more illumination sources which are positioned on one side of the gap and a light detector which is positioned on the other side of the gap, facing the illumination sources. For example, the in-vivo device may be device 10 or device 300. The device may further comprise an imager and a broad band white light illumination source on the other end of the device, opposite the side containing the gap. The method may comprise illuminating in-vivo fluids at different wavelengths (720) and measuring transmission spectra of the in-vivo fluids (730). A processor either within the device or external to it may perform comparison of the transmission spectra of the in-vivo fluids to a predetermined transmission spectrum of bile (740), thereby determining the concentration of bile (750). According to the concentration of bile in each location in-vivo, the processor may perform the step of determining a location of the in-vivo device in a segment resolution at each point of the transmission spectra (760). In some embodiments, a processor either within the device 10 or 300 or external to it, or an external user, e.g., a physician, may perform the steps of determining the in-vivo location of the device. The method may further comprise determining the presence of blood according to the transmission spectra, such that it may be determined whether blood is present in-vivo and in what location. In other embodiments, instead of comparing between transmission or absorption spectra, the method may comprise comparing between processed discrete signals detected by the light detector and a predetermined threshold, as will be described in detail with reference to FIGS. 11-12.

Other methods of localization may use an imager and white light opposite the end of the device containing a gap, such that an in-vivo image may indicate the location in-vivo, along with the determination regarding the presence of blood. In other embodiments, the device may include a pH detector such that, based upon the pH level detected, a location of the device along the GI tract may be determined. In yet other embodiments, the localization of the device may be done using spectral information of bile, while the spectral information of blood may indicate the presence of blood in-vivo, and in-vivo images may show the source of the bleeding on the tissue if any.

Figure 8:
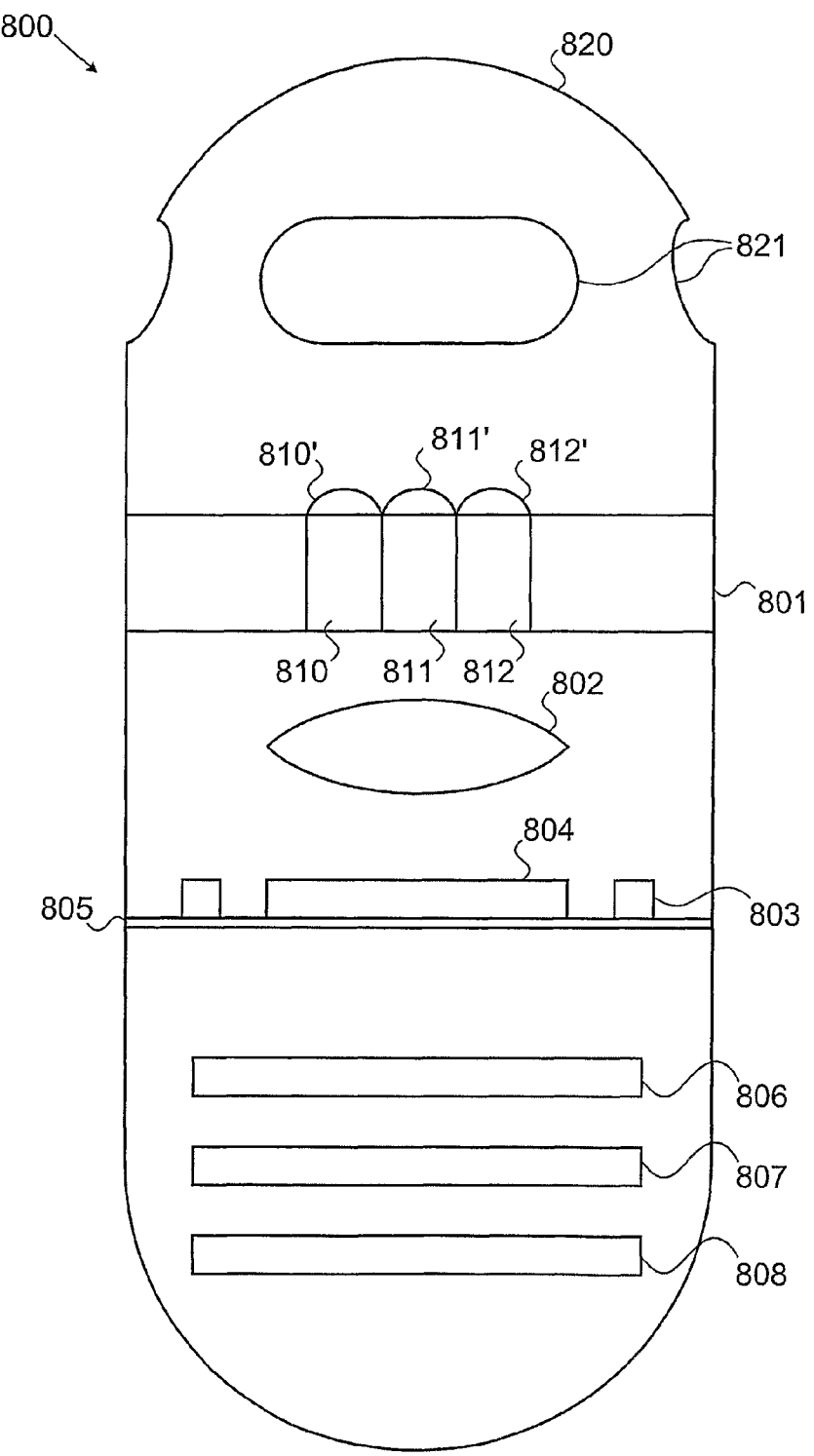
FIG. 8 is a schematic illustration of a device for the detection of bleeding in-vivo in accordance with another embodiment of the present invention.

Reference is now made to FIG. 8 which is a schematic illustration of a device for the detection of bleeding in-vivo in accordance with another embodiment of the present invention. According to embodiments of the present invention, an in-vivo sensing device 800 comprises a reacting substrate 801. Reacting substrate 801 may be located perpendicularly to the longitudinal axis of device 800. Above the reacting substrate 801 may be an opaque cover 820, located perpendicularly to the longitudinal axis. Opaque cover 820 pushes the lumen wall away from reacting substrate 801 and in addition provides better isolation for reacting substrate 801 from the in vivo surroundings.

Opaque cover 820 assists in isolating data sensed in device 800 from data which may be sensed from the surroundings without the presence of opaque cover 820. By having an opaque cover 820 rather than a transparent one (for example, as in known swallowable imaging capsules), device 800 has the ability to sense and collect information of reactions occurring within device 800 alone, without any interference from reactions occurring externally to device 800. This assists in achieving a high signal to noise ratio.

The opaque cover 820 comprises at least two openings 821 to allow continuous flow of in-vivo fluids through the body of device 800. According to some embodiments, the shape of openings 821 may be one that induces the flow of in-vivo fluids through them, e.g., the shape of a truncated cone, where the base of the cone is at the interface between device 800 and the in-vivo surrounding, and its diameter is decreased as entering further into device 800. This could increase the concentration of fluids passing through device 800 and so increase the quantity of in-vivo markers carried within the in vivo fluids which freely flow through the at least two openings 821 into the space created within opaque cover 820. According to some embodiments, a mirror may replace opaque cover 820.

Reacting substrate 801 may have attached thereon at least one type of binding agent, e.g., antibodies or other suitable peptides. The binding agent is typically specific to or has a high affinity to a desired in-vivo marker which indicates the presence of blood in-vivo. The binding agents attached should withstand the GI environment, e.g., withstand the presence of bile and other acidic or alkaline environments according to the location it would be exposed to along the GI tract.

For example, the in-vivo markers may be globin A and globin B which are protein moiety of Hemoglobin, or the protein glycophorin A which is one of the proteins located on the membrane of erythrocytes. Such proteins or protein moiety may bind to the binding agents attached onto the reacting substrate 801. According to some embodiments, reacting substrate 801 may be divided into more than one section, for example, sections 810, 811 and 812. Each of these sections may have attached thereon at least one type of binding agent suitable to bind a marker indicating the presence of blood. In some embodiments, each section of reacting substrate 801 may comprise a different coating, e.g., section 810 may be coated with coating 810', section 811 may be coated with coating 811', and section 812 may be coated with coating 812'. In some embodiments, the coatings are designed to degrade together or to degrade separately during passage of the device 800 through the GI tract, under specific in-vivo environment conditions, e.g., certain pH level, under specific enzymatic activity, after a predetermined time period, etc. For example, coating 810' may be designed to degrade in the stomach environment, coating 811' may be designed to degrade in the small bowel environment and coating 812' may degrade in the colon.

For example, when device 800 reaches the stomach, coating 810' may degrade since it is in contact with the environment of the stomach. When the device 800 continues its way along the GI tract, it reaches the small bowel. Coating 811', for example, may be made of a material that withstands the low pH present in the gastric juice (pH around 3). However, at a higher pH level (pH above 5.5), the material of coating 811' may degrade and thus enable fee flow of in-vivo fluids near reacting substrate section 811 such that the in-vivo markers may bind to the binding agents attached onto section 811. Other small bowel specific materials may be used, for example, time dependent materials which are designed to degrade after a predetermined time period which corresponds with the transit time of the device 800 through the stomach until it reaches the small bowel. Further examples for materials which may be used may depend on enzymatic reactions which are small intestine dependent, etc.

The device 800 may further pass along the GI tract and reach the colon. When the device reaches the colon, the coating 812' may degrade and colon fluids carrying in-vivo markers indicating presence of blood may bind to the binding agents attached to section 812. The degrading of the coating 812' may be pH dependent. Examples for pH dependent coatings, which degrade only in a pH above 5.5 may be made of methacrylic acid copolymers, i.e., Eudragit® polymers, which have a variety of grades such that each type of Eudragit® polymers degrade at different pH level. Other enteric polymers may include polyvinyl acetate phthalate, hydroproxypropyl methylcellulose phthalate, cellulose acetate phthalate, and cellulose acetate trimelliate, or a combination thereof.

Other coating materials dedicated to degrading in the colon may be polymers which degrade in the presence of colon bacteria or due to enzymatic reaction which is colon specific. For example, using biodegradable polymers or azo polymers in coatings designed to degrade in the colon is efficient, since they degrade by the azoreductase enzymes produced by the azobacters present in the colon. Other materials may be time dependent, such that they are designed to degrade or degrade after a predetermined time period that corresponds to the transit time of the device 800 through the small bowel until it reaches the colon.

In-vivo sensing device 800 is exposed to the in-vivo surroundings. Reacting substrate 801 is exposed to in-vivo fluids flow and may thus be exposed to in-vivo markers flowing within the in-vivo fluids. This constant exposure may aid in achieving binding at high concentrations, of a desired in vivo marker to the binding agents in the different sections 810, 811 and 812.

According to some embodiments, a sensor 804 is positioned with a view of the reacting substrate 801, so that an optical change occurring on the reacting substrate 801 may be detected by the sensor 804. The optical change may be a change of color, a change of hue, a change of brightness, a change of intensity, a change of optical density, a change of light transmissivity, a change of light scattering or any combination thereof.

The optical change occurring on reacting substrate 801 and sensed by sensor 804 is one which may occur due to a structural change in either the binding agent or in the in-vivo marker bound to it, or in both.

According to some embodiments, reacting substrate 801 may be fabricated from various materials that are suitable for immunoassay, e.g., silicon, glass, plastic, etc. Parameters to be considered while assessing if a material is suitable for manufacturing reacting substrate 801, may be, for example, the material's transparency, its safety for internal use, its durability under endo-luminal conditions, and so on. Therefore, any material known in the art for manufacture of a biological substrate for attaching a binding agent thereon may be suitable. According to some embodiments, reacting substrate 801 may be a transparent lab-on chip type substrate, which would allow various reactions to take place on it, and to be sensed by sensor 804. According to other embodiments, composites such as polystyrene are also suitable for constructing reacting substrate 801.

In some embodiments, device 800 may comprise an optical system 802 which may typically comprise a lens. The lens focuses the optical change onto sensor 804. Optical change may be, for example, the illumination emitted from the binding agent attached onto reacting substrate 801. In some embodiments, optical system 802 is designed only for focusing illumination emitted from a predetermined distance, which may be the distance between optical system 802 and reacting substrate 801. When optical system 802 is designed as such, illumination emitted from farther distances would not be focused onto sensor 804 and would not be sensed by it, and so background noise is substantially avoided.

In some embodiments, device 800 comprises at least one illumination source 803. According to some embodiments, sensor 804 and illumination source 803 may face said reacting substrate 801 such that rays from the illumination source 803 impinge on the reacting substrate 801, and are then reflected to the sensor 804. According to some embodiments, the area of reacting substrate 801, onto which the binding agents are attached, is of a size correlating to the size of sensor 804, so that the information from reacting substrate 801, would be detected in its entirely by sensor 804, without any missed data.

Typically, in one embodiment, illumination source 803 is a white LED. According to other embodiments, illumination source 803 may be a monochromatic illumination source. In some embodiments, there may be more than one monochromatic illumination source. According to other embodiments, there may be more than one illumination source 803, each of which may have a different illumination spectrum.

According to some embodiments, each illumination source 803 having a different spectra may illuminate either the same type of binding agents attached onto reacting substrate 801 in each section or may illuminate more than one type of binding agent attached in each of the sections 810, 811 and 812. When illuminating with more than one illumination source 803, each having different spectra of illumination, sensor 804 may receive various reflections at different illumination spectra. In some embodiments, the variety of reflections may provide additional information on pathology that might be present in the living body. The sensed optical change occurring due to binding of in-vivo markers to binding agents, when there is one type of binding agents, may provide information on one type of pathology, e.g., bleeding in-vivo. Whereas, when there is more than one type of binding agents, the optical changes occurring due to binding of the different in-vivo markers to their different corresponding binding agents may provide information on various types of pathologies, e.g., presence of blood and presence of markers indicating colorectal cancer.

In some embodiments, in order to detect the presence of an in vivo marker indicating pathology, there may be a need to initiate binding of a tagged binding agent to the marker. According to some embodiments, following binding of the in vivo marker to the binding agent, which is attached onto reacting substrate 801, in each section, an additional binding agent, for example an antibody, may be inserted into the body lumen. This inserted binding agent is typically specific to or has a high affinity to the desired in-vivo marker, typically to a different site on the marker's structure, than the site where the binding agent attached on reacting substrate 801 is bound. The inserted binding agent may be tagged, for example with gold particles, beads or a tagging molecule which may exhibit fluorescence, as further disclosed in U.S. Patent Application Publication No. 2009/0312631, published on Dec. 17, 2009. Therefore, in some embodiments, following binding of the in vivo marker to the binding agent attached to reacting substrate 801, the tagged binding agent may bind to the marker at a different site, creating a complex of binding agents, markers and tagged binding agents. In some embodiments, when the device 800 has reached the stomach, for example, the coating 810' degrades and thus enables the binding of the tagged binding agent to the marker which binds to the binding agent attached onto section 810. When reacting substrate 801, onto which the complex is attached, is illuminated, sensor 804 may detect an optical change indicating the different bound molecules and, thus, indicating the presence of blood.

According to some embodiments, the binding agent administered into the body lumen, may be inserted by drinking, swallowing, injecting, etc. The insertion of the binding agent may be done following insertion of device 800 into the body. In some embodiments, device 800 may be inserted into the body, and, after a given time period, which may allow degrading of the coating covering a certain section in reacting substrate 801 and may allow binding of the desired in vivo marker to the binding agent on the reacting substrate 801, the tagged binding agent would be inserted into the body. In other embodiments, the tagged binding agent is administered at substantially the same time as when the device 800 is inserted in-vivo. In other embodiments, the tagged binding agent may be administered prior to the insertion of device 800.

According to some embodiments, the inserted binding agent may be tagged with gold particles, beads, molecules exhibiting fluorescence or any other tagging technique which may be noticeable when illuminated. When the binding agent is tagged with, for example, gold particles or beads, it may be noticed when illuminated in wavelengths of visible light. When, for example, the binding agent is tagged with a fluorescence emitting tagging molecule, the binding agent may be noticeable when illuminated in spectra suitable for inducing fluorescence, e.g., illumination in an ultraviolet spectrum may cause emission in visible light spectrum.

Reacting substrate 801 may be continuously viewed by sensor 804, such that a long exposure time may be achieved. This is an important feature especially when an optical change detected is fluorescence related. In fluorescence, the number of photons absorbed by the molecule illuminated is greater than the number of photons emitted from it. Therefore, in order to obtain a high signal, there is a need to sense a substantially static image, such as sensing a reacting substrate 801, which is constantly in contact with in vivo fluids, and is continuously viewed for optical changes.

The in vivo marker may be carried within the in vivo fluids which freely flow near device 800, assuming blood is present in-vivo.

According to some embodiments, sensor 804 may comprise pixels that are larger than the pixels typically used for imagers, such as CCD or CMOS imager. For example, sensor 804 may comprise pixels of up to 100 microns.

According to some embodiments, at least one illumination source 803 and sensor 804 are placed on a PCB 805. Typically, device 800 may be autonomous and may comprise an internal power source 806, e.g., silver-oxide batteries. According to other embodiments, device 800 may be connected to an external power source through wires or cables.

According to some embodiments, device 800 may comprise a transmitter 807 to transmit the data sensed by sensor 804 to a receiver external to the device 800. In some embodiments, transmitter 807 may include a wireless transmitter, e.g., able to transmit Radio Frequency (RF) signals or other types of communication signals. For example, transmitter 807 may transmit wireless signals utilizing an antenna 808. Other wireless methods of transmission may be used.

A system, according to some embodiments of the invention, may include an in-vivo sensing device 800, transmitting information (e.g., images and/or other data) to a data receiver and/or recorder possibly close to or worn on a subject. A data receiver and/or recorder may of course take other suitable configurations. The data receiver and/or recorder may transfer the received information to a larger computing device, such as a workstation or personal computer, where the data may be further analyzed, stored, and/or displayed to a user. In other embodiments, each of the various components need not be required and or may be housed in alternate configurations; for example, an internal device may transmit or otherwise transfer (e.g., by wire) information directly to a viewing or processing system. In another example, the data receiver or workstation may transmit or otherwise transfer information to the in-vivo device. While in one embodiment the device may be an autonomous capsule, other configurations, such as an endoscope or trocar may be used.

According to some embodiments, device 800 may be a swallowable capsule. According to other embodiments, device 800 may be capsule shaped or may be of any other shape such as a sphere, an ellipsoid, a peanut, etc. In other embodiments, opaque cover 820 need not be of a dome shape, but rather may be, for example, flat.

Figure 9:
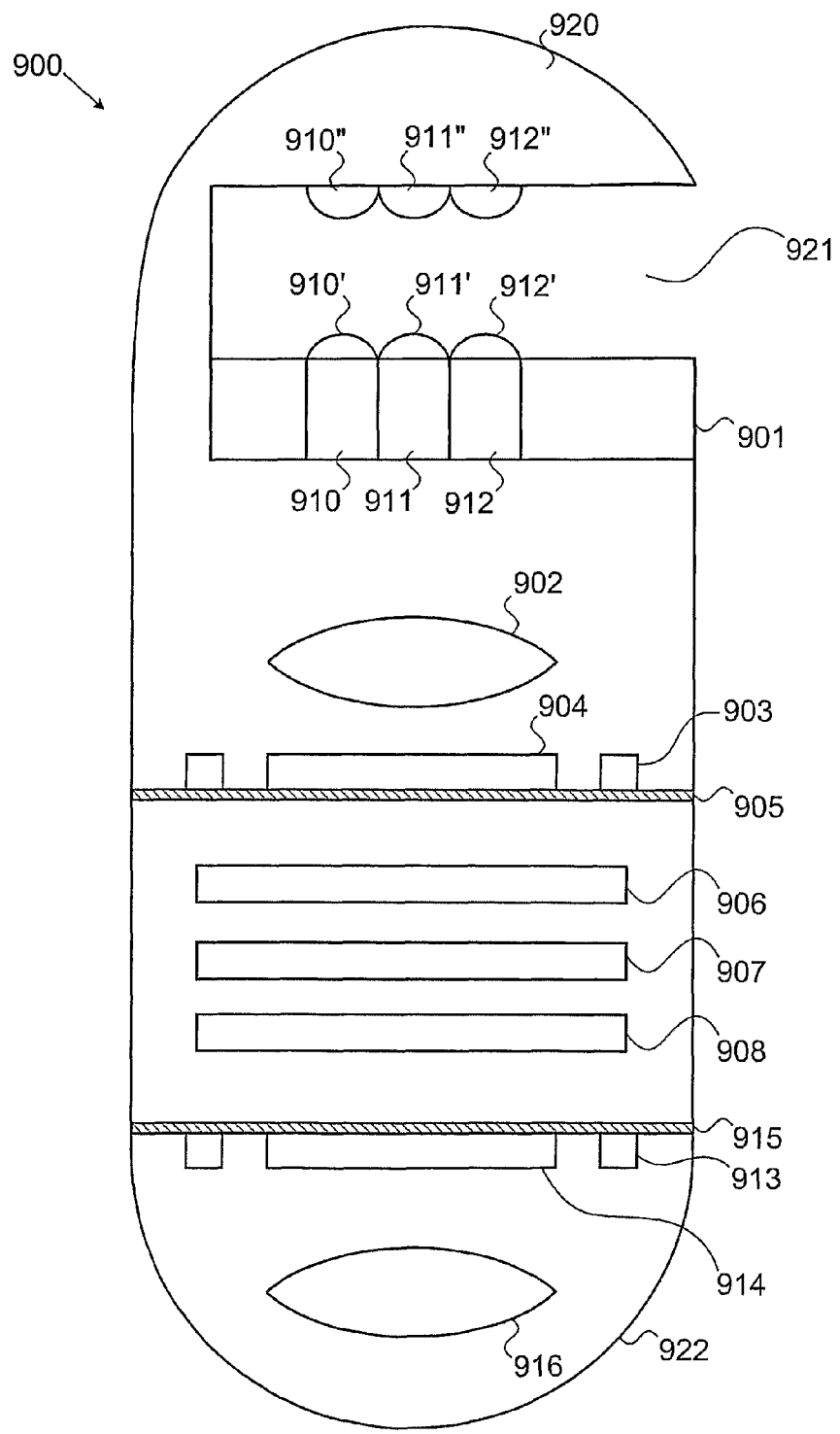
FIG. 9 is a schematic illustration of a device for the detection of bleeding in-vivo in accordance with yet another embodiment of the present invention.

Reference is now made to FIG. 9 which is a schematic illustration of a device for the detection of bleeding in-vivo in accordance with yet another embodiment of the present invention. According to embodiments of the invention as described in FIG. 9, in-vivo device 900 is similar to device 800 but with the addition of another sensing head 922. According to some embodiments, an image sensor 914 is positioned at an end of device 900, opposite the end of sensor 904 that is behind dome 920. Thus, in this embodiment, the device 900 has two ends, an end, covered by dome 920, for blood/bile analysis as discussed above, and an end 922 for imaging.

Image sensor 914 may be used for imaging the lumen into which device 900 is inserted. In some embodiments, imager 914 may be a CCD or CMOS imager, with pixel size of, for example, 5-6 microns. According to some embodiments, imager 914 may acquire images of the body lumen, whereas sensor 904 senses an optical change due to binding of in-vivo marker to a binding agent. Therefore, data of the location in a lumen, in which a pathology is present, may be acquired using image sensor 914.

According to some embodiments, imager 914 may acquire images simultaneously with signal acquisition by sensor 904, or may acquire images sequentially with signal acquisition by sensor 904. According to some embodiments, imager 914 may be controlled by a user, e.g., a physician. For example, a physician may receive sensed data from sensor 904 in real-time and, when an optical change is sensed, the physician may activate imager 914 to acquire images of the lumen at the location of the optical change. In some embodiments, a physician may activate sensor 904 according to an image acquired by image sensor 914, which may indicate in-vivo bleeding.

According to other embodiments, imager 914 and/or sensor 904 may be activated automatically in response to an image or other optical data sensed by the other sensor (sensor 904 or imager 914, respectively). Image analysis or other recognition algorithms may be used in this embodiment. An image may be analyzed on board the device or in an external device (such as in a receiver), and a command may be sent to the required sensor (sensor 904 or imager 914) based on the analysis.

According to some embodiments, there may be provided at least one illumination source 913, to illuminate a lumen into which device 900 is inserted. In some embodiments, in front of image sensor 914 there may be provided an optical system 916 to focus illumination reflected from the lumen onto imager 914 for image acquisition. According to some embodiments, image sensor 914 and optical system 916 may be designed as disclosed in U.S. Patent Application Publication No. 2007/0118018, published on May 24, 2007.

According to some embodiments, device 900 may be autonomous and may comprise an internal power supply 906, e.g., a silver-oxide battery. Device 900 may comprise more than one battery 906, or may be externally powered, for example by power induction to the battery or through wires or cables to an external power source.

In some embodiments, device 900 may comprise a transmitter 907. Transmitter 907 may transmit data sensed by sensor 904, image data acquired by imager 914, or both. In some embodiments, device 900 may comprise more than one transmitter for transmitting data acquired by device 900. There may be one transmitter for transmitting data sensed by sensor 904 and one transmitter for transmitting image data acquired by imager 914. According to some embodiments, transmitted data may be transmitted to an external receiver (not shown). The external receiver may receive data simultaneously from the at least two transmitters.

According to some embodiments, instead of separate administration to the patient of a tagged binding agent, which should bind to the in-vivo marker, device 900 may include additional cells 910", 911" and 912" that may contain the tagged binding agents, corresponding to reacting substrate sections 910, 911 and 912, respectively. Cells 910", 911" and 912" may be positioned opposite of the respective reacting substrate sections 910-912. Cells 910"-912" may be coated with the same coating as coatings 910', 911' and 912', respectively. This ensures release of the specific tagged binding agents at the correlating location where the coating over the specific reaction substrate section is degraded.

For example, when device 900 reaches the stomach, the coating 910' is degraded. At the same time, the coating over cell 910" is degraded, since it is also designed to degrade at the stomach. In other embodiments, the cell designed to detect blood in the stomach may not be coated at all, since the stomach is practically the first organ which the device passes through. After coating 910' degrades, the reacting substrate section 910 may be in contact with stomach fluids, as may the tagged binding agents in cell 910". When an in-vivo marker indicating the presence of blood is present in the stomach fluids, for example, globin A, globin B or glycophorin A, this in-vivo marker binds to the binding agent on reacting substrate section 910. Then, the tagged binding agent released from cell 910" may bind to the bound marker and may then be detected by sensor 904. The same may take place in section 911 when device 900 reaches the small bowel, for example, when coating 911' is degraded along with the coating of cell 911". And again, it may occur in section 912 when device 900 reaches the colon, for example, and coating 912' degrades along with the coating on cell 912", such that an optical change may be detected by sensor 904 indicating blood in-vivo.

According to some embodiments, device 900 may be a swallowable capsule. According to other embodiments, device 900 may be of a capsule shape or of any other shape such as a sphere, an ellipsoid, a peanut, etc.

Figure 10:
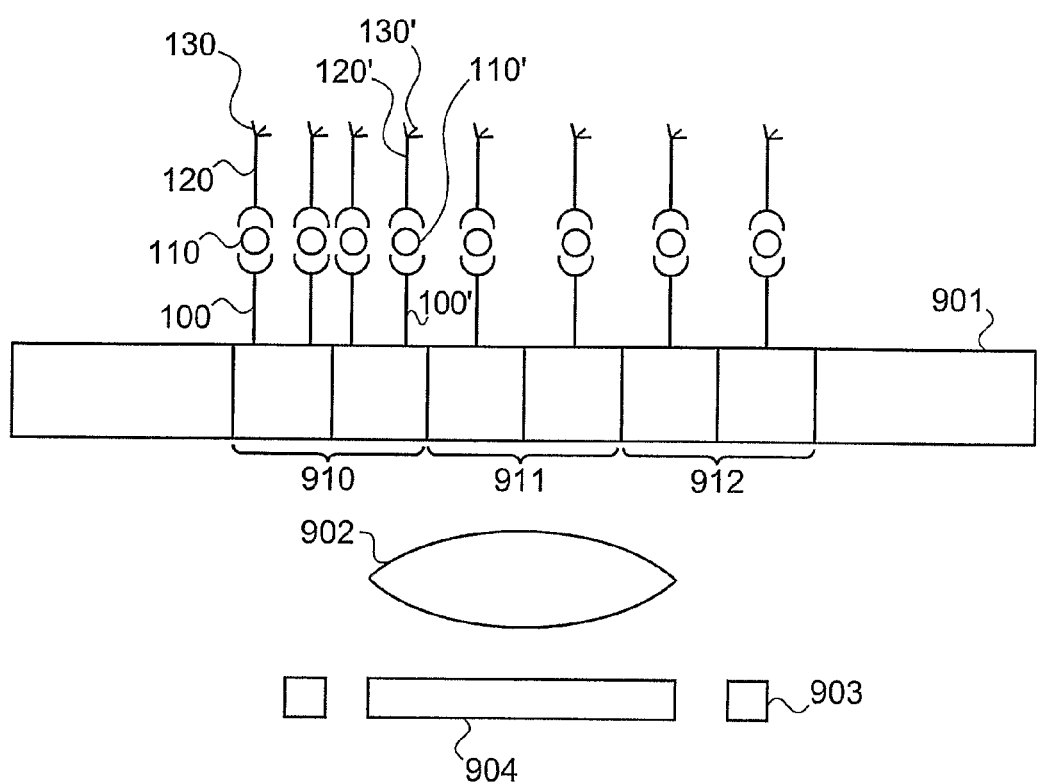
FIG. 10 is a schematic illustration of a section of a device for the detection of bleeding in-vivo in accordance with one embodiment of the present invention.

Reference is now made to FIG. 10, which is a schematic illustration of a section of a device for the detection of bleeding in-vivo in accordance with one embodiment of the present invention. FIG. 10 shows a larger view of the reacting substrate 901 according to certain embodiments of the invention. According to some embodiments, there may be more than one type of binding agents attached onto reacting substrate 901 at each of the sections 910, 911 and 912.

In some embodiments, binding agent 100 is attached onto reacting substrate 901, and in-vivo marker 110 binds to binding agent 100. The binding between binding agent 100 and in-vivo marker 110 may cause a structural change in binding agent 100, in in-vivo marker 110 or in both, which may lead to an optical change. In some embodiments, there may be an additional binding agent 100' of a different kind, either to bind the same marker or to bind a different marker indicating the presence of blood in-vivo. Binding agent 100' binds in-vivo to marker 110' (which may or may not be the same as marker 110) which may lead to a structural change in binding agent 100', in in-vivo marker 110' or in both, which may lead to an optical change.

In other embodiments, for example in section 910, binding agent 100 is attached on reacting substrate 901, and in-vivo marker 110 binds to reacting substrate 901. Binding agent 120 tagged with a tag 130 is either administered into the lumen from outside of the patient (e.g., by swallowing or injection) or may be released from a cell within device 900, and then binds to the in-vivo marker 110, which is already immobilized on reacting substrate 901. When reacting substrate 901 is illuminated, tag 130 may be noticeable and may be detected by sensor 904. This may occur at the same way in each of the sections of reacting substrate 901, e.g., sections 910, 911 and 912 in one or more types of binding agents. In some embodiments, for example, in section 910, binding agent 100' is attached on reacting substrate 901, and in-vivo marker 110' binds to it. Binding agent 120' tagged with a tag 130' is either administered into the lumen from outside of the patient (e.g., by swallowing or injection) or may be released from a cell within device 900, and then binds to the in-vivo marker 110', which is already immobilized on reacting substrate 901. When reacting substrate 901 is illuminated, tag 130' may be noticeable and may be detected by sensor 904.

According to some embodiments, transmitter 807 or 907 may transmit the data detected to an external receiver (not shown). This receiver may be a disposable receiver as described in FIG. 5 above. In some embodiments, the receiver may be a wearable disposable patch. A patient may wear the receiver and may swallow a new device 800 or 900 every day for a week, for example, in order to monitor the in-vivo environment to detect bleeding. This is because bleeding may not always be a constant pathology, but rather may be active on one day, may stop for a day or two, and may be noticed again on a different day. Therefore, there may be a need to monitor the bleeding over an extended period of time, e.g., a week, by inserting into the patient a new device every day for a week. The receiver may include a visual indication which may show where along the GI tract blood was detected. For example, the receiver may include different LEDs corresponding to various locations along the GI tract, e.g., esophagus, stomach, small bowel and colon. The LEDs may light up when a detection of bleeding is made by the sensors 814 or 914. For example, if blood is detected in the small bowel, the LED corresponding to the small bowel may light up indicating to the patient and/or the physician the patient's condition. In other embodiments, there may be other methods of indicating to the patient and his physician the patient's condition. In yet other embodiments, the indication may be encoded so that the patient's medical condition would not be clear to him, but rather the physician alone would know how to read the indication. This may be useful in order to prevent the patient from being anxious and worried if he would be able to see and understand the results of the procedure.

According to some embodiments, the device used for the detection of bleeding in-vivo may be a combination of devices 10 or 300 and device 800 or 900. The device used for detection of bleeding may be a combination of a device which may detect light signals, e.g., perform spectral analysis (e.g., devices 10 or 300), and in addition detect blood by using immunoassay based analysis (e.g., devices 800 or 900). When the combined device enters the colon, for example, solids floating in the colon fluids may block the gap 12 (FIG. 1A) or 312 (FIG. 3) located on one end of the combined device, such that no signal may be detected. Therefore, adding a device performing immunoassay on the opposite end of the combined device would ensure the detection of blood by either spectral analysis or immunoassay analysis or both.

According to some embodiments, in-vivo devices 800 or 900 may be combined with in-vivo devices 10 or 300, such that one end of the combined in-vivo device would be similar to the end of device 800 or 900, which comprises a reacting substrate (801 or 901), while the other end of the combined device would be similar to the end of either of devices 10 or 300, which comprises a gap (12 or 312) and illumination sources and light detectors facing each other and located on opposite sides of the gap. Such a combined in-vivo device would be able to detect through one end (the end similar to devices 10 or 300) spectral signals transmitted and reflected from the in-vivo fluids flowing through the gap, and would be able to detect through an opposite end (the end similar to device 800) signals reflected from markers (e.g., proteins) flowing in the in-vivo fluids. The combined in-vivo device may have two ways through which blood presence may be detected: (a) through light signals of illuminated fluids flowing in and out of a gap located on one end of the combined device, and (b) through light signals of illuminated tagged markers (e.g., proteins) that have bound to tagging agents attached onto an opposite end of the combined device. According to some embodiments, the combined in-vivo device may detect spectral signals and protein related signals (providing immunoassay analysis), which may enable a more accurate analysis and determination regarding the presence of blood in-vivo.

According to some embodiments, devices 800 and 900 may comprise a gel or hydrogel covering the openings in the opaque cover 820 and 920 respectively. A hydrogel may allow the flow of fluids through the openings 821, 921 of devices 800 and 900 respectively, but may block solids which flow in in-vivo fluids from entering the device 800 and 900. The hydrogel may serve as a blocker for solids, which prevents them from blocking the openings and such allow free flow of in-vivo fluids. This is essential since the fluids carry with them the markers indicating presence of blood.

In other embodiments, devices 800 and 900 may comprise hydrogel filling the entire space created by opaque cover 820 and 920 covering the reacting substrates 801 and 901, respectively. In these embodiments, the hydrogel may fill the entire space through which in-vivo fluids are supposed to enter and exit devices 800 and 900. The hydrogel may prevent entrance of solids into the device 800 and 900 and allow passage of only fluids through it.

According to some embodiments, devices 10 and 300 may also comprise a hydrogel coating over the gap 12 and 312 respectively. The hydrogel may either be coated above or under the environment specific coatings or fillings 312a-312c. The hydrogel may ensure blocking of solids from entering the gap (12 or 312) and thus allowing light to pass through in-vivo fluids and be detected by light detector (14 or 314). The hydrogel may only allow passage of fluids in and out of it such to enable blood detection with no interference.

Figure 11:
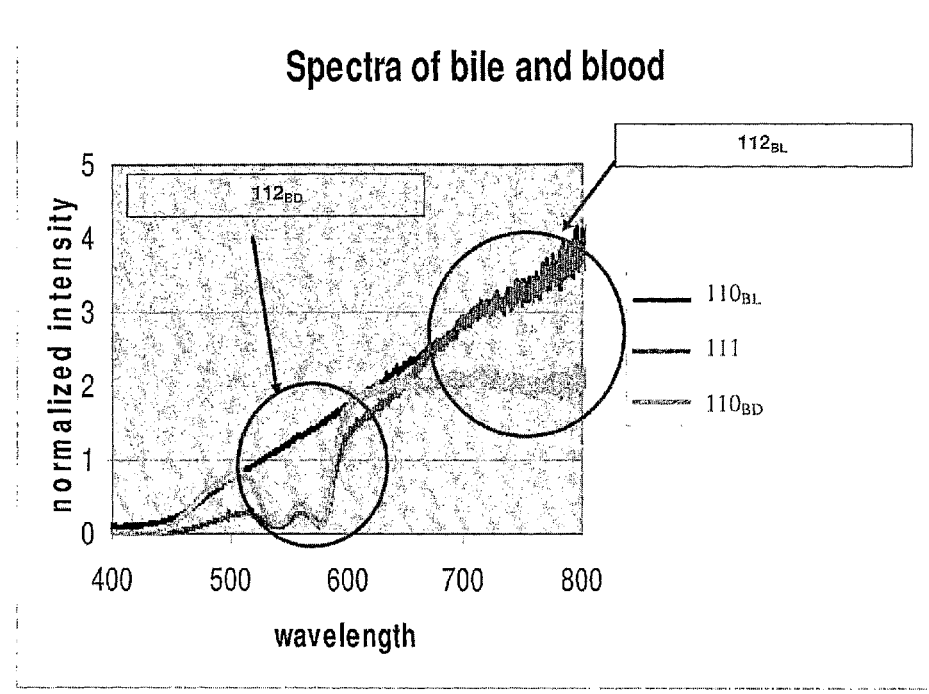
FIG. 11 is a graph illustrating the spectra of blood in water, of bile and of blood in bile in accordance with an embodiment of the present invention.

Reference is now made to FIG. 11, which is a graph illustrating the spectra of blood in water ($110_{BD}$), of bile ($110_{BL}$) and of blood in bile (111) in accordance with an embodiment of the present invention. According to the graph in FIG. 11, blood in water absorbs light with substantially high specificity at wavelengths between 400 nm to 650 nm, and more specifically between 500-650 nm circled on the graph in circle $112_{BD}$. However, the spectra of bile $110_{BL}$ at wavelengths of 400-650 nm is very similar to the spectra of blood in water $110_{BD}$. This makes it difficult to distinguish between presence of blood and bile, i.e. it may be difficult to differentiate between the presences of blood from bile according to readings of light intensity at wavelengths of 400 nm to 650 nm alone. There is therefore a need for more readings at other wavelengths. According to the graph in FIG. 11, blood in water does not absorb light at wavelengths of 650 nm to 900 nm; the slope of $110_{BD}$ is constant at wavelengths of 650-900 nm, whereas bile does absorb light at those same wavelengths—the slope of $110_{BL}$ is increasing at 650-900 nm. This area of the bile spectra, and more specifically between 700-800 nm is circled on the graph in circle $112_{BL}$.

According to the present invention, a "blood score" and a "bile score" are calculated in order to differentiate between the presence of blood in-vivo and the presence of bile. According to the present invention, the "blood score" may be calculated from at least two readings measuring light intensity in at least two different wavelengths selected from 400-650 nm (which are the wavelengths at which blood absorbs light at high specificity), whereas the "bile score" may be calculated from at least two readings detecting light intensity in at least two different wavelengths selected from 650-900 nm (which are the wavelengths at which bile absorbs light at high specificity).

According to an embodiment of the invention, the in-vivo device 10 or 300 may comprise several, for example, four different illumination sources (e.g. LEDs). Two of the four illumination sources may illuminate at two different wavelengths selected from 400 nm to 650 nm, while the last two illumination sources may illuminate at two different wavelengths selected from 650 nm to 900 nm. For example, the at least four illumination sources may illuminate at: 560 nm, 610 nm, 700 nm and 800 nm. The "blood score" may be calculated from the ratio of detected light that is illuminated by one illumination source illuminating at 560 nm and another illumination source illuminating at 610 nm, whereas the "bile score" may be calculated from the ratio of detected light that is illuminated by one illumination source illuminating at 700 nm and another illumination source illuminating at 800 nm. If the ratio from the readings of 560 nm and 610 nm is zero, i.e. the spectra is a flat line, it may be concluded that the illuminated fluid flowing in and out of the gap (12 or 312) contains no blood. If the ratio from the readings of 700 nm and 800 nm is zero, i.e. the spectra is a flat line, it may be concluded that the illuminated fluid contains no bile.

Figure 12:
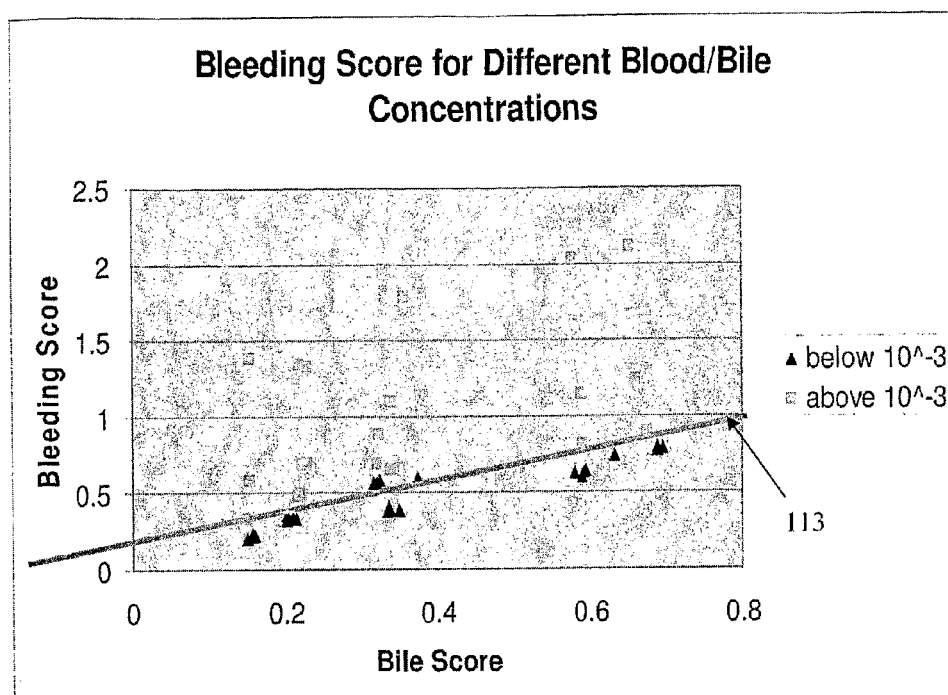
FIG. 12 is a graph illustrating the threshold for determining presence of blood in-vivo, in accordance with one embodiment of the present invention.

Reference is now made to FIG. 12, which is a graph illustrating the threshold for determining presence of blood in-vivo, in accordance with one embodiment of the present invention. After calculating the "blood score" and the "bile score" from four readings of light detector 14 or 314, resulting from light being illuminated in four different wavelengths, (e.g. 560 nm, 610 nm, 700 nm and 800 nm), and passing through in-vivo fluids flowing in and out of device 10 or 300, there is a need to determine whether the detected signals indicate on a blood concentration caused by an in-vivo pathology, or whether the blood concentration is considered to be in the normal range. Typically a blood concentration of $10^{-3}$ [liter of blood/liter of fluids] is considered to indicate on a pathology. Therefore the calculated readings may be compared with a predetermined threshold 113, which may indicate whether the readings indicate blood concentration of above or below $10^{-3}$ [liter of blood/liter of fluids].

According to FIG. 12, the graph is created from the combination of the "blood score" and the "bile score" for every four readings. The "bile score" is represented in the X axis and the "blood score" is represented in the Y axis, thereby creating from every four readings a point with (x, y) coordinates. For example, "blood score" is created by the ratio of light intensity at 560 nm and 610 nm, whereas "bile score" is created by the ratio of light intensity at 700 nm and 800 nm. A point on the graph that has (x, y) coordinates is created from the scores as such: (x="bile score", y="blood score"). The scores must be calculated for four readings detected at substantially the same time period such that they represent readings at substantially the same in-vivo location.

Each point in the graph may be compared with a predetermined and pre-calculated threshold 113, which shows the correlation between the "blood score" and the "bile score" that results in blood concentration of $10^{-3}$ [liter of blood/liter of fluids]. Predetermined threshold 113 may assist in determining whether or not every four readings indicate on blood concentration that is above $10^{-3}$ [liter of blood/liter of fluids] and which indicates on a pathology. Any point on the graph in FIG. 12 that is above threshold 113 may indicate that the blood concentration is above $10^{-3}$ [liter of blood/liter of fluids] in the in-vivo location where the readings of that point took place, i.e. a pathology is present around that in-vivo location. Any point below threshold 113 may indicate that the blood concentration is below $10^{-3}$ [liter of blood/liter of fluids] in the in-vivo location where the readings of that point took place, i.e. no pathology is present around that in-vivo location.

Threshold 113 may be calculated, for example, from in-vitro experiments during which light intensity at different wavelengths is detected for bile in water of various concentrations, and light intensity at different wavelengths is detected for blood in water of various concentrations. As can be seen from FIG. 11, when the illuminated fluid contains bile and blood (spectra 111), the presence of bile causes the blood in water spectra ($110_{BD}$) to be of a lower slope, i.e. the substantially high specificity of absorption by blood ($110_{BD}$) of light at wavelengths between 400-600 nm is not as high when in the presence of bile. Therefore, the predetermined threshold 113 is an increasing threshold; the higher the bile concentration, the higher the threshold is.

According to some embodiments of the present invention, the at least four illumination sources (e.g. 560 nm, 610 nm, 700 nm, 800 nm) may illuminate all at once, which would require four separate light detectors with four separate filters, each light detector having thereon a different filter. However, in other embodiments, the four illumination sources may illuminate one subsequent to the other, such that one light detector may detect light that passed through the in-vivo fluids from one illumination source at a time. In any case, four readings from the four different illumination sources, at substantially the same time, are needed in order to determine blood presence in-vivo (or blood concentration), at substantially the same in-vivo location.

According to some embodiments, the graphs illustrated in FIG. 11 and FIG. 12 may be created during a processing process that may be done within the in-vivo device 10 or 300. In other embodiments, the processing may be done by a unit located externally to the in-vivo device, e.g. by a receiver 52 or by a processing unit 54, as shown in FIG. 5. In the embodiments where the processing is done within the in-vivo device, and the device includes four different illumination sources and only one light detector, the in-vivo device should include a memory unit. The signals detected by the light detector from every four readings (of the four illumination sources) at substantially the same time, which correlates to substantially the same in-vivo location, may be stored in the in-vivo device's memory, and only after four readings have been detected would the blood and bile scores be calculated and compared with the predetermined threshold.

According to some embodiments, instead of illuminating at four different wavelengths, an indication of blood presence in-vivo may be done with only two illumination sources. The two illumination sources may illuminate at different wavelengths selected from wavelengths where the bile spectra is linear, i.e. at 650-900 nm (FIG. 11). For example, one illumination source may illuminate at 700 nm and another illumination source may illuminate at 610 nm. The processing method of the detected light signals may comprise creating a linear plot from the two points, which intersects with the X axis. The detected light intensities corresponding to the illuminated wavelengths may create two points on a plot. The X axis of the plot may be the wavelength of the illumination sources and the Y axis may be the detected light intensity. If the intersection with the X axis occurs around 450 nm, which is also the intersection of bile spectra ($110_{BL}$) with the X axis (FIG. 11), then it may be determined that there is only bile in the illuminated in-vivo fluids, and no blood present. That is, the plot created from the two points is in fact a plot of bile spectra. However, if the intersection with the X axis occurs at a higher wavelength, it may be determined that there is blood in the illuminated in-vivo fluids.

According to other embodiments, three different illumination sources may be used to illuminate in-vivo fluids flowing through the devices 10 or 300. The processing method may comprise creating a plot from two points corresponding to two illumination sources as described above, and comparing a third point from a third illumination source to the created plot. The X axis of the plot may be the wavelength of the illumination source and the Y axis of the plot may be the detected light intensity corresponding to the illuminated wavelength. For example, an illumination source illuminating at 700 nm and an illumination source illuminating at 610 nm may be used to create two points on the plot, which intersects with the X axis, as described above. The location of a third point, corresponding to a third illumination source illuminating at a wavelength selected from wavelengths at which blood absorbs light at high specificity, i.e. at 400-650 nm, may be compared with the plot. For example, the third illumination source may illuminate at 560 nm. If the light intensity of the third point (e.g. intensity at 560 nm) is located on the created plot, it may be determined that there is only bile and no blood in the illuminated in-vivo fluids. If the third point is located below the plot, i.e. the third point is located between the plot and the X axis, it may be determined that there is blood in the illuminated in-vivo fluids. The farther the third point is from the created plot, and the closer it is to the X axis, the higher the blood concentration at the illuminated in-vivo fluids.

It will be appreciated that the present invention is not limited to what has been particularly shown and described hereinabove. Rather the scope of the present invention is defined only by the claims which follow.

What is claimed is:

1. An in-vivo sensing system for detecting blood comprising:
   an in-vivo sensing device comprising:
      a housing having a capsule portion and having a first portion and a second portion protruding from, and integrally formed with, said capsule portion,
      said first and second portions defining therebetween a gap that is external to said capsule portion of said housing and is configured to allow in-vivo fluids to flow freely through the gap, wherein said first portion and said second portion are on opposing sides of the gap;
      said first portion enclosing an illumination source configured to emit light at a narrow band illumination wavelength into the gap and illuminate the in-vivo fluids flowing therethrough;
      said second portion enclosing a light detector positioned on an opposing side of the gap from, and facing across the gap towards, the illumination source, and configured for detecting light that passed from the illumination source, across the gap and through the in-vivo fluids flowing therein;
      a transmitter for transmitting signals detected by the light detector;
   a receiver for receiving the detected signals; and
   a processing unit for comparing the detected signals to a predetermined threshold thereby determining the presence of bile and blood in-vivo.

2. The system according to claim 1 further comprising:
   an illumination source for illuminating broad band illumination; and
   an imager for acquiring images in-vivo, wherein said broad band illumination source and said imager are positioned on one end of the device opposite the end comprising the illumination source, the gap and the detector.

3. The system according to claim 1, comprising at least two illumination sources, wherein said illumination sources operate in an alternating mode with different pulse duration.

4. The system according to claim 1, wherein said system comprises light detectors at a number corresponding to the number of illumination sources, wherein each light detector detects light from a corresponding illumination source that faces it.

5. The system according to claim 4, wherein illumination from the illumination sources passes through a collimator before passing through the in-vivo fluids, such that each light detector detects light only from its corresponding illumination source that faces it.

6. The system according to claim 4, wherein each light detector comprises a filter to allow passage of light at a specific wavelength illuminated from its corresponding illumination source.

7. The system according to claim 6, wherein said filters are selected from a group consisting of narrow band filters, interference filters and diffractive optical element filters.

8. The system according to claim 1, wherein said in-vivo device is a swallowable capsule.

9. The system according to claim 1,
wherein said gap is divided into more than one cell, wherein each of the more than one cell comprises said illumination sources; and
wherein each of the cells is coated with a different enteric-coating that degrades in response to a sensed parameter.

10. The device according to claim 9, wherein degradation of said enteric coating in response to a sensed parameter occurs at a predetermined in-vivo location.

11. The device according to claim 9, wherein the sensed parameter is a parameter selected from a group consisting of: pH, bacteria, and enzyme activity.

12. The device according to claim 9, wherein said device is a swallowable capsule.

13. The system according to claim 1, wherein the gap is defined in an external surface of said housing.

14. The system according to claim 1, wherein said distal end of each of said first portion and said second portion protruding from said housing are not attached to each other, such that in-vivo fluids may flow freely into and out of the gap between said distal ends.

15. A method for detecting blood in-vivo comprising:
inserting an in-vivo sensing device into the GI tract of a patient, wherein said device comprises:
a housing having a capsule portion and having a first portion and a second portion protruding from, and integrally formed with, said capsule portion,
said first and second portions defining therebetween a gap that is external to said capsule portion of said housing and is configured to allow in-vivo fluids to flow freely through the gap, wherein said first portion and said second portion are on opposing sides of the gap;
said first portion enclosing at least one illumination source, each of said at least one illumination source configured to emit light at a different narrow band illumination wavelength into the gap and illuminate the in-vivo fluids flowing therethrough; and
said second portion enclosing at least one light detector, each of said at least one light detector positioned on an opposing side of the gap from, and facing across the gap towards, the at least one illumination source, and configured for detecting light that passed from the illumination source, across the gap and through the in-vivo fluids flowing therein;
illuminating in-vivo fluids at different wavelengths;
detecting light signals that pass through the in-vivo fluids of the different wavelengths;
processing the detected light signals;
comparing the processed light signals with a predetermined threshold; and
determining the presence of blood in the in-vivo fluids.

16. The system according to claim 15, wherein said distal end of each of said first portion and said second portion protruding from said housing of said device are not attached to the other, such that in-vivo fluids may flow freely into and out of the gap between said distal ends.

17. A method for localizing an in-vivo sensing device in segment resolution along the gastrointestinal (GI) tract, the method comprising:
inserting an in-vivo sensing device into the GI tract of a patient, wherein said device comprises:
a housing having a capsule portion and having a first portion and a second portion protruding from, and integrally formed with, said capsule portion,
said first and second portions defining therebetween a gap that is external to said capsule portion of said housing and is configured to allow in-vivo fluids to flow freely through the gap, wherein said first portion and said second portion are on opposing sides of the gap,
said first portion enclosing at least two illumination sources configured to emit light at a different narrow band illumination wavelength into the gap and illuminate the in-vivo fluids flowing therethrough,
said second portion enclosing at least one light detector positioned on an opposing side of the gap from, and facing across the gap towards, a respective one of the at least two illumination sources, and configured for detecting light that passed from the illumination source, across the gap and through the in-vivo fluids flowing therein;
illuminating in-vivo fluids at different wavelengths;
measuring transmission spectra of the in-vivo fluids;
comparing the transmission spectra of the in-vivo fluids to a predetermined transmission spectra of bile;
determining the concentration of bile; and
determining a location of the in-vivo device in a segment resolution at each point of the transmission spectra.

18. The method according to claim 17, wherein determining a location of the in-vivo device further comprises determining whether the device is in a segment selected from a group consisting of: a stomach, small bowel or colon.

19. The method according to claim 18, wherein said in-vivo device further comprises of a pH detector for detecting pH along the GI tract.

20. The method according to claim 18, wherein determining a location of the device is done by determining the concentration of bile along with determining the pH along the GI tract.

21. The method according to claim 18, further comprising determining the presence of blood according to the transmission spectra.

22. The method according to claim 17, wherein the gap is defined in an external surface of said housing.

23. The system according to claim 17, wherein said distal end of each of said first portion and said second portion protruding from said housing of said device are not attached to each other, such that in-vivo fluids may flow freely into and out of the gap between said distal ends.

* * * * *